US011789024B2

(12) United States Patent
de Carvalho Lains et al.

(10) Patent No.: US 11,789,024 B2
(45) Date of Patent: Oct. 17, 2023

(54) BIOMARKERS FOR AGE-RELATED MACULAR DEGENERATION

(71) Applicant: Massachusetts Eye and Ear Infirmary, Boston, MA (US)

(72) Inventors: Ines Maria de Carvalho Lains, Cambridge, MA (US); Deeba Husain, Lexington, MA (US); Joan W. Miller, Winchester, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 774 days.

(21) Appl. No.: 16/612,099

(22) PCT Filed: May 9, 2018

(86) PCT No.: PCT/US2018/031878
§ 371 (c)(1),
(2) Date: Nov. 8, 2019

(87) PCT Pub. No.: WO2018/208970
PCT Pub. Date: Nov. 15, 2018

(65) Prior Publication Data
US 2021/0116461 A1    Apr. 22, 2021

Related U.S. Application Data

(60) Provisional application No. 62/503,721, filed on May 9, 2017.

(51) Int. Cl.
*G01N 33/68* (2006.01)
*G01N 33/50* (2006.01)

(52) U.S. Cl.
CPC ..... *G01N 33/6848* (2013.01); *G01N 33/5038* (2013.01); *G01N 2800/16* (2013.01)

(58) Field of Classification Search
CPC .......... G01N 33/6848; G01N 33/5038; G01N 2800/16
See application file for complete search history.

(56) References Cited

U.S. PATENT DOCUMENTS

| | | | |
|---|---|---|---|
| 6,012,058 | A | 1/2000 | Fayyad et al. |
| 6,615,205 | B1 | 9/2003 | Cereghini et al. |
| 2007/0197436 | A1 | 8/2007 | Thacker |
| 2008/0160505 | A1 | 7/2008 | Hollyfield et al. |

FOREIGN PATENT DOCUMENTS

| | | |
|---|---|---|
| WO | WO 2011/162589 A1 | 12/2011 |
| WO | WO 2017/066529 A1 | 4/2017 |

OTHER PUBLICATIONS

[No Author Listed],"The age-related eye disease study system for classifying age-related macular degeneration from stereoscopic color fundus photographs: the age-related eye disease study report No. 6," American Journal of Opthalmology, 2001, 132(5):668-681.
Borgatti, "How to explain hierarchical clustering,"Connections, 1994, 17(2): 78-80.
Burgess et al., "Metabolome-wide association study of primary open angle glaucoma," Investigate Opthalmology & Visual Science, 2015, 56(8):5020-5027.
Chakravarthy et al., Clinical risk factors for age-related macular degeneration: a systematic review and meta-analysis. BMC Ophthalmol, Jan. 2010;10:31.
D'Andrade, "U-Statistic Hierarchical Clustering," Psychometrika, Mar. 1978, 43(1): 59-97.
Danis et al., "Methods and reproducility of grading optimizied digital color fundus photographs in the age-realted eye disease study 2 (AREDS2 report No. 2)," Invest Ophthalmol & Visual Science, Jul. 2013, 54(7):4548-4554.
Evans et al., "Antioxidant vitamin and mineral supplements for slowing the progression of age-related macular degeneration," Cochrane Database of Systematic Reviews, 2012, (7):1-108.
Evans et al., "High resolution mass spectrometry improves data quantity and quality as compared to unit mass resolution mass spectrometry in high-throughput profiling metabolomics," Metabolomics: Open Acces, Jan. 2014, 4(2):1-7.
Fiehn., "Metabolomics—the link netween genotypes and phenotypes," Plant Molecular Biology, Jan. 2002, 48(1-2): 155-171.
Food and Drug Administration. "FDA approves new drug treatment for age-realted macular degeneration," 2012, 2 pages.
Johnson, "Hierarchical Clustering Schemes" Psychometrika, 32(3):241-254.
Kanungo et al., "An efficient k-means clustering algorithm: Analysis and implementation," IEEE Transctions on Pattern Analysis and Machine Intelligence, Jul. 2002, 24(7):881-892.
Lains et al., "Human plasma metabolomics study across all stages of age-related macular degeneration identifies potential lipid biomarkers," American Academy of Opthalmology, Feb. 2018, 125(2); abstract only.
MacKay, "Information theory, inference and learning algorithms," Cambridge University Press, 2003, pp. 432-433.
Mazzone et al., "Metabolite profiles of the serum of patients with non-small cell carcinoma," Journal of Thoracic Oncology, Jan. 2016, 11(1):72-78.
Meads et al., "Clinical effectiveness and cost-utility of photodynamic therapy for wet age-related macular degeneration: a systematic review and economic evaluation," Health Technology Assessment, 2003, 7(9): 1-4.
Mitta et al., "C-reactive protein and the incidence of macular degeneration: pooled analysis of 5 cohorts," JAMA Ophthalmol, Apr. 2013, 131(4):507-513.
Moja et al., "Systemic safety of bevacizumab versus ranibizumab for neovascular age-related macular degeneration," Cochrane Database of Systematic Reviews, 2014, (9):1-61.
Motsinger-Reif et al., "Comparing metabolomic and pathologic biomarkers alone and in combination for discriminating alzheimer's disease from normal cognitive aging," Acta Neuropathologica Communications, 2013, 1(28):1-9.

(Continued)

*Primary Examiner* — Ruixiang Li
(74) *Attorney, Agent, or Firm* — Fish & Richardson P.C.

(57) ABSTRACT

This disclosure relates to biomarkers for Age-Related Macular Degeneration (AMD) and methods of use thereof, e.g., methods of the use of biomarkers for determining that a subject has Age-related Macular Degeneration (AMD) or determining the stage of AMD in a subject.

14 Claims, 6 Drawing Sheets

(56) References Cited

OTHER PUBLICATIONS

Nicholson et al., "Metabolic phenotyping in clinical and surgical environments," Nature, Nov. 15, 2012, 491(7424):3 84-3 92.
PCT International Preliminary Report on Patentability in International Appln. No. PCT/US18/031878, dated Oct. 1, 2018, 7 pages.
PCT International Search Report and Written Opinion in International Appln. No. PCT/US18/31878, dated Oct. 1, 2018, 15 pages.
Shlens, "A tutorial on principal component analysis," Google Research, Apr. 7, 2014, 1-12.
Smith, "A tutorial on principal components analysis," Univerisity of Otago, Feb. 26, 2002, 1-28.
The Elements of Statistical Learning, 2nd ed., Hastie et al. (ed)., 2001, p. 95-100.

BIOMARKERS FOR AGE-RELATED MACULAR DEGENERATION

CROSS-REFERENCE TO RELATED APPLICATIONS

This application is a 371 U.S. National Phase Application of PCT/US2018/031878, filed on May 9, 2018, which claims the benefit of U.S. Application No. 62/503,721, filed on May 9, 2017, which is incorporated by reference herein in its entirety.

TECHNICAL FIELD

This disclosure relates to biomarkers for Age-Related Macular Degeneration (AMD) and methods of use thereof.

BACKGROUND

Age-related Macular Degeneration (AMD) is the leading cause of adult blindness in developed countries. Worldwide, it ranks third, and is expected to affect 288 million people by 2040. Even when it does not cause blindness, AMD often leads to central vision distortions and significant impairment in patients' quality of life.[2] The natural history of AMD typically comprises "dry" early and intermediate forms, which can progress to atrophic (geographic atrophy, GA) and/or neovascular lesions (choroidal neovascularization, "wet" AMD) in some subjects (Sobrin et al., Nature and nurture-genes and environment-predict onset and progression of macular degeneration. Prog Retin Eye Res. 2013 Dec. 27; Yonekawa et al., Age-Related Macular Degeneration: Advances in Management and Diagnosis. J Clin Med. 2015 January; 4(2):343-59).

AMD is usually asymptomatic in its early stages and diagnosed only on routine eye exam, thus remaining often undetected until it is more advanced leading to visual symptoms. It is critical to develop tools of detecting AMD earlier and slow the progression of degeneration to the blinding untreatable atrophic forms of the disease. Therefore, there is a great need to find easily accessible screening tools for diagnosis of this disease.

SUMMARY

The disclosure provides methods of determining whether a subject has AMD. The methods include performing mass spectrometry on a body fluid sample, such as blood, urine, or ocular fluid, to determine the amount of a set of metabolites in the sample, and determining whether the subject has AMD.

In one aspect, the disclosure provides methods of determining whether a subject has Age-related Macular Degeneration (AMD). The methods include obtaining a sample, e.g., a bodily fluid sample, from a subject; performing mass spectrometry on the sample to determine the amount of a set of metabolites in the sample; applying a principle component algorithm to a dataset derived from the level of the set of metabolites, thereby obtaining a value corresponding to one or more principle components for the subject; and determining that the subject has AMD. In some embodiments, the determination if followed by a therapeutic step.

In some embodiments, the set of metabolites includes one or more metabolites in Table 5, one or more metabolites in Table 6, or one or more metabolites in Table 7. In various embodiments, the sample is a blood sample, a blood serum sample, a urine sample, a vitreous humour sample, or an aqueous humour sample.

The disclosure also provides methods of determining the stage of AMD in a subject. The methods include obtaining a sample, e.g., a bodily fluid sample, from a subject; performing mass spectrometry on the sample to determine the amount of a set of metabolites in the sample, wherein the set of metabolites includes 1-stearoyl-2-oleoyl-GPC, 1-linoleoyl-2-arachidonoyl-GPC, stearoyl-arachidonoyl-glycerol, oleoyl-oleoyl-glycerol, dihomo-linolenoylcarnitine, 1-stearoyl-2-arachidonoyl-GPC, linoleoyl-linolenoyl-glycerol, 1-stearoyl-2-linoleoyl-GPI, N2-methylguanosine, oleoyl-linoleoyl-glycerol, oleoylcarnitine, ximenoylcarnitine, or 1-stearoyl-2-arachidonoyl-GPI; and determining the stage of AMD in the subject.

In some embodiments, the set of metabolites includes one or more metabolites in Table 8. In various embodiments, the bodily fluid sample is a serum sample, a urine sample, a vitreous humour sample, or an aqueous humour sample. In some embodiments, the stage of AMD is determined by principle component analysis, regression analysis, or clustering analysis.

In another aspect, the disclosure also provides methods of determining that a subject has AMD by obtaining a sample, e.g., a bodily fluid sample, from a subject; performing mass spectrometry on the sample to determine the amount of a set of metabolites in the sample; and determining that the amount of one or more metabolites selected from the group consisting of linoleoyl-arachidonoyl-glycerol, stearoyl-arachidonoyl-glycerol, oleoyl-arachidonoyl-glycerol, oleoyl-arachidonoyl-glycerol, 1-palmitoyl-2-arachidonoyl-GPC, and 1-stearoyl-2-arachidonoyl-GPC is lower than a reference value; or determining that the amount of adenosine is higher than a reference value; and determining that the subject has AMD.

In some embodiments, the set of metabolites includes one or more metabolites in Table 5, one or more metabolites in Table 6, or one or more metabolites in Table 7. In some embodiments, the bodily fluid sample is a serum sample, a urine sample, a vitreous humour sample, or an aqueous humour sample.

In other aspects, the disclosure provides methods of determining and treating a subject having AMD by determining the subject has AMD by any methods described in this disclosure; and administering a treatment to the subject. In some embodiments, the treatment includes administering an anti-VEGF agent to the subject, or administering an antioxidant vitamin to the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
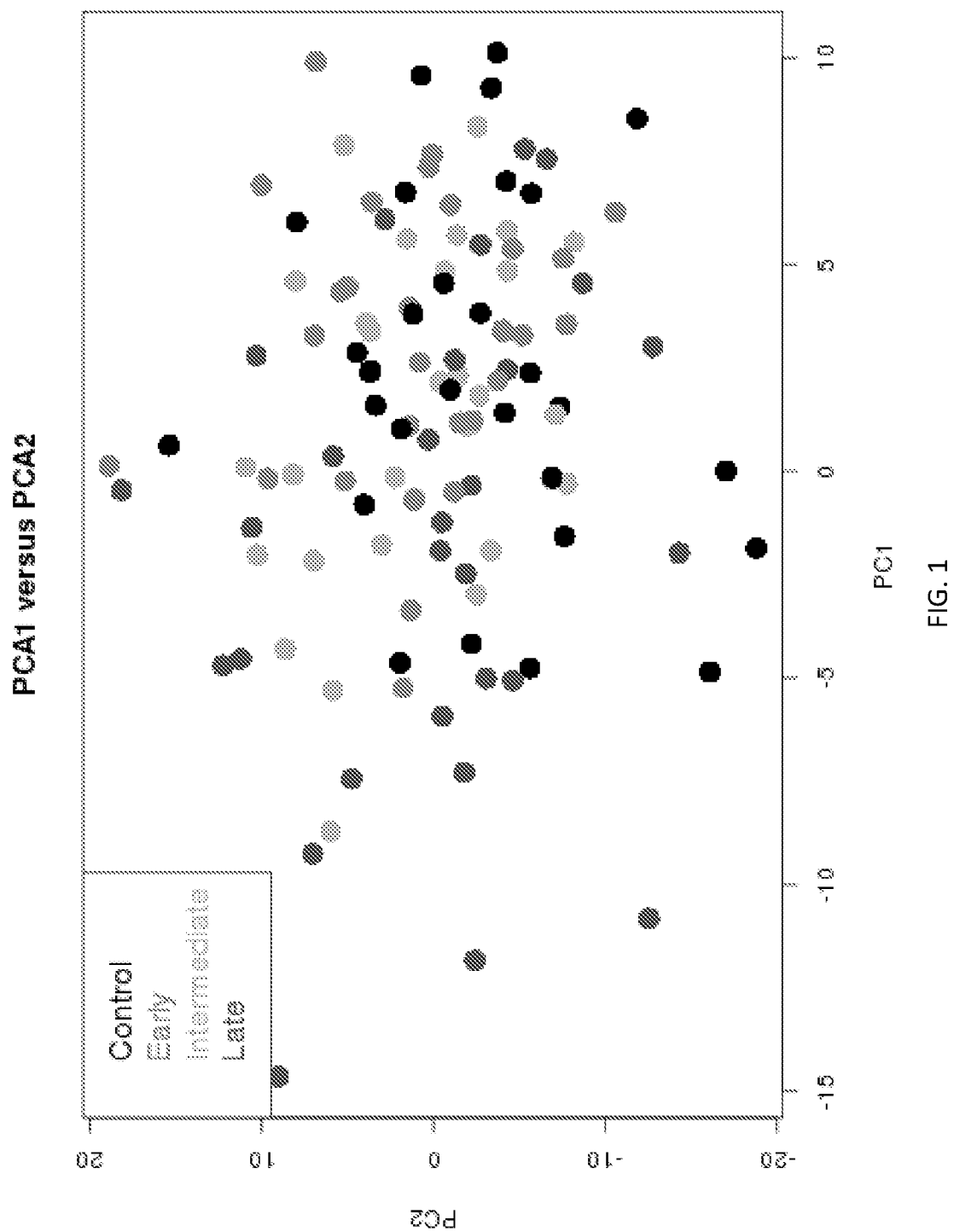
FIG. 1 is a graph of scatter plot of PC1 and PC2 with controls and AMD groups.

Age-related Macular Degeneration is the leading cause of adult blindness in developed countries. As AMD is usually asymptomatic in its early stages and diagnosed only on routine eye exam, one purpose of the present disclosure is to find new potential biomarkers for Age-Related Macular Degeneration (AMD).

Biomarkers are measurable indicators of the severity or presence of a disease and can be of many types. They can be elements identified in the serum or urine. Serological biomarkers have been sought and researchers have primarily focused their search on biomarkers related to inflammation and lipid levels (Mitta et al., C-reactive protein and the incidence of macular degeneration: pooled analysis of 5 cohorts. JAMA Ophthalmol. 2013 April; 131(4):507-13; Chakravarthy et al., Clinical risk factors for age-related macular degeneration: a systematic review and meta-analysis. BMC Ophthalmol. 2010 January; 10:31). However, reliable and accessible biofluid biomarkers for AMD have still not been found. Metabolomics, the global profiling of all the small molecules (<1 kDa) comprising a biological system, is a novel approach that is increasingly being explored to derive biomarkers (Fiehn O. Metabolomics—the link between genotypes and phenotypes. Plant Mol Biol. 2002 January; 48(1-2):155-71). Metabolites are the downstream product of the cumulative effects of the genome and its interaction with environmental exposures (Nicholson et al., Metabolic phenotyping in clinical and surgical environments. Nature. 2012 Nov. 15; 491(7424):384-92). Therefore, the metabolome is thought to closely represent the "real functional state" of the biological system and therefore current disease phenotype.

The value of metabolomics as a translational tool for the clinical setting has been demonstrated through several studies in other medical disciplines, including cancer and prenatal diseases. Metabolomics platforms can be applied to accessible biological samples, such as blood and urine, and mass spectroscopy (MS) provides high sensitivity and selectivity for metabolites present in such body fluids.

The present disclosure characterizes the plasma metabolomic signatures of patients with AMD and subjects with no known AMD; and also evaluates metabolomic signatures of the different stages of AMD (early, intermediate, and late disease) using MS-based metabolomics.

Using a broad-based MS platform, the plasma metabolomic profiles of a cohort of patients with AMD were assessed and compared to subjects with healthy maculae. After controlling for age, gender, body mass index (BMI), and smoking status, 87 metabolites significantly distinguished AMD cases from controls. Indeed, when the first principal component of these 87 metabolites was included as a model predictor, the ability to discriminate AMD cases increased, as compared to a baseline model that only included clinical covariates. Of these metabolites, over half (48 metabolites) also differed significantly across AMD severity stages. Consistently, both for the comparison between AMD versus controls and the different stages of AMD, the vast majority of the identified significant metabolites are involved in lipid metabolism, in particular glycerophospholipid metabolism. These metabolites include stearoyl-arachidonoyl-glycerol, a diacylglycerol, and 1-stearoyl-2-arachidonoyl-glycerophosphacholine, a phosphatidylcholine.

This disclosure also validates a significant role for alanine and aspartate metabolism, and a role for the glycosphingolipids' pathway. The examples described in the present disclosure were prospectively designed, and all data collection was standardized. In addition, participants underwent a complete ophthalmologic exam performed by a retina specialist, ensuring excellent phenotypic characterization. This is particularly important since many other studies of metabolomics rely on established repositories and databases, which often lack good phenotypic information particularly for ophthalmic disease. The samples were collected fasting and processed immediately (within 30 minutes) and frozen at −80 degree. Metabolomic profiling, which was performed using a state of the art platform that covers a wide-range of the metabolome and identifies metabolites using a chemocentric approach with standards for each identified metabolite.

The data in the present disclosure supports the relevance of lipid-related metabolites in AMD. In particular, the findings point to a significant deregulation in the glycerophospholipid pathway among individuals with AMD. Glycerophospholipids are a main component of cell membranes, including neural membranes, accounting for up to 25% of the dry weight of the adult brain. They provide structural stability and membrane fluidity. They also participate in the formation of ion channels and receptors, generation of second messengers in signal transduction, and regulating neurotransmitter release. Four major classes of glycerophospholipids provide stability, and are required for proper functioning of neural membranes; these include diacylglycerophospholipids, plasmalogens, alkyl-acyl-glycerophospholipids and phosphatidylcholine. The fatty acids required for glycerophospholipids synthesis in the central nervous system (CNS) are transported from the gastrointestinal tract (coming from the diet or being produced by the liver). Glycerophospholipids have recognized roles in maintaining cell membrane integrity, forming ion channels and receptors, and regulating neurotransmitter release. Additionally, the metabolites of glycerophospholipids (together with sphingolipids) seem to play an important role in initiating and maintaining oxidative stress in neurologic disorders, as well as in neural cell proliferation, differentiation, and apoptosis.

The photoreceptors and the RPE are rich in phospholipids, which are important for the transduction of visual stimuli. This disclosure reveals that metabolites linked to the key glycerophospholipids, such as diacylglycerols and phosphatidylcholines, are lowered in subjects with AMD, suggesting that an impaired cell membrane structure and function might be a component of AMD pathogenesis. The observed depletion in glycerophospholipids in AMD patients may result from decreased levels of parent molecules, a change in metabolism or lipid peroxidation. Decreased levels of parent molecules could happen locally in the eye or elsewhere in the body since the fatty acids required for synthesis in the central nervous system (CNS) are transported from the gastrointestinal tract (coming from the diet or being produced by the liver). Altered catabolism could occur because of a change in phospholipases, the enzymes responsible for the catabolism of glycerophospholipids in the CNS and the retina.

Phospholipase C is involved in the regulation of phototransduction, and is responsible for the hydrolyzation of phospholipids into inositol 1,4,5-triphosphate and diacylglycerol.

Phospholipase A2 is another phospholipase that seems to play a role in apoptosis, inflammation and neurodegeneration. One of the catabolic metabolites of phospholipase A2 is glycerol-phosphocholine, a metabolite that was decreased in subjects with AMD.

Age-Related Macular Degeneration (AMD)

Age-Related Macular Degeneration is a medical condition which may result in blurred or no vision in the center of the visual field. AMD is usually asymptomatic in its early stages and diagnosed only on routine eye exam, thus remaining often undetected until it is more advanced leading to visual symptoms. Over time, however, some patients may experience a gradual worsening of vision that may affect one or both eyes. AMD usually does not result in complete blindness, but the loss of central vision can make it hard to recognize faces, drive, read, or perform other activities of daily life.

In AMD, there is a progressive accumulation of characteristic yellow deposits, called drusen (buildup of extracellular proteins and lipids) in the macula between the retinal pigment epithelium and the underlying choroid. Thus, AMD can be divided into 3 stages: early, intermediate, and late, based partially on the extent (size and number) of drusen. The methods of classifying and grading AMD are described, e.g., in The Age-Related Eye Disease Study system for classifying age-related macular degeneration from stereoscopic color fundus photographs: the Age-Related Eye Disease Study Report Number 6. Am J Ophthalmol. 2001 November; 132(5):668-81; Danis R P, Domalpally A, Chew E Y, Clemons T E, Armstrong J, SanGiovanni J P, et al. Methods and reproducibility of grading optimized digital color fundus photographs in the Age-Related Eye Disease Study 2 (AREDS2 Report Number 2). Invest Ophthalmol Vis Sci. 2013 July; 54(7):4548-54, each of which is incorporated by reference in its entirety.

In the most recent Age-Related Eye Disease Study 2 (AREDS2) definitions, the standard disc diameter equals 1800 µm (rather than 1500 µm), which affects the size of the Early Treatment Diabetic Retinopathy Study (ETDRS) grid and of the standard drusen circles; and that geographic atrophy (GA) is present if the lesion has a diameter equal or greater than 433 µm (AREDS circle 1-2) and has at least two of the following features—absence of RPE pigment, circular shape, or sharp margins (foveal involvement not a requirement). With these criteria, AMD can be divided into different stages:
 (1) Healthy controls (AREDS stage 1)—presence of drusen maximum size<circle C0 and total area<C1;
 (2) Early AMD (AREDS stage 2)—drusen maximum size≥C0 but <C1 or presence of AMD characteristic pigment abnormalities in the inner or central subfields;
 (3) Intermediate AMD (AREDS stage 3)—presence drusen maximum size≥C1 or of drusen maximum size≥C0 if the total area occupied was >I2 for soft indistinct drusen and >O2 for soft distinct drusen;
 (4) Late AMD (AREDS stage 4)—presence of GA according to the criteria described above or evidence of neovascular AMD.

For subjects with different severity stages in the two eyes (e.g. early AMD in one eye and intermediate in the other eye), in some embodiments, the more advanced stage is assumed.

AMD is also characterized as "atrophic" or "neovascular," the former showing loss of outer retinal layers, and the latter showing the presence of choroidal neovascularization (CNV). Neovascular (or "wet") AMD is defined by the formation of abnormal blood vessels that grow from the choroidal vasculature, through breaks in Bruch's membrane, toward the outer retina. These blood vessels are immature in nature and leak fluid below or within the retina. The two forms of AMD can occur together and share pathologies of cell death and fibroglial replacement. Neovascular AMD accounts for 10 to 15% of AMD cases, develops abruptly, and rapidly leads to substantial loss of vision. Although growth factors appear to play an important role in the late stage of neovascular AMD progression, they likely do not contribute to the underlying cause of the disease.

Current standard of care for patients with AMD involves targeting the proangiogenic and permeability molecule vascular endothelial growth factor-A (VEGF). These anti-VEGF agents include, e.g., Bevacizumab, Ranibizumab, Conbercept. Other approved antiangiogenic drugs include pegaptanib and aflibercept. These anti-VEGF agents and the methods of treating AMD are described, e.g., in Moja, Lorenzo et al., "Systemic safety of bevacizumab versus ranibizumab for neovascular age-related macular degeneration," The Cochrane Library (2014); and US Food and Drug Administration. "FDA approves new drug treatment for age-related macular degeneration." (2012), each of which is incorporated by reference in its entirety.

Photodynamic therapy has also been used to treat wet AMD. The drug verteporfin is administered intravenously; light of an appropriate wavelength is then applied to the abnormal blood vessels. This activates verteporfin to destroy the blood vessels. The photodynamic therapy is described, e.g., in Meads, Catherine, et al. "Clinical effectiveness and cost-utility of photodynamic therapy for wet age-related macular degeneration: a systematic review and economic evaluation." (2003), which is incorporated herein by reference in its entirety.

Furthermore, laser coagulation can also be used to treat wet AMD. Antioxidant vitamins (e.g., beta-carotene, vitamin C and vitamin E) and mineral supplements (e.g., zinc) can slow the progression of AMD. The methods of slowing AMD progression by antioxidant vitamin and mineral supplements is described, e.g., in Evans, Jennifer R., and John G. Lawrenson, "Antioxidant vitamin and mineral supplements for slowing the progression of age-related macular degeneration," The Cochrane Library (2012), which is incorporated by reference in its entirety.

Subjects

In any of the methods described herein, a subject may be either a human or a non-human animal. In some embodiments, the subject has not been diagnosed as having AMD, but may have a family history of AMD, or may be at an age when screening for AMD is recommended. In some embodiments of any of the methods described herein, the subject has been identified as having AMD (e.g., a subject has early AMD, intermediate AMD, or late AMD).

A subject in any of the methods described herein can be a child, an adolescent, a teenager, or an adult (a subject that greater than 18 years old, e.g., greater than 20 years old, greater than 25 years old, greater than 30 years old, greater than 35 years old, greater than 40 years old, greater than 45 years old, greater than 50 years old, greater than 55 years old, greater than 60 years old, greater than 65 years old, greater than 70 years old, greater than 75 years old, greater than 80 years old, greater than 90 years old, or greater than 100 years old). In some embodiments, an AMD screening test is recommended for subjects who are 50 years old, and the screening test should be done every one or two years thereafter.

In any of the methods described herein, the subject may have an increased risk of developing AMD (e.g., the subject has a family history of AMD). Therefore, the present disclosure provides methods of detecting and diagnosing AMD for subjects with an increased risk of developing AMD.

In some embodiments, the subject is being treated for AMD. Thus, the present disclosure provides methods of monitoring the effectiveness of the treatments. In some embodiments, the methods include the steps of determining the amount of a group of appropriate metabolites in the sample, and comparing the amount of metabolites before, during, and/or after treatment, thereby monitoring the effectiveness of the treatment.

In some embodiments, the methods described herein can be used to determine whether a subject can recover from AMD and/or how the disease may progress in a particular patient. In some cases, the methods include the steps of determining the amount of a group of appropriate metabolites in the sample from the subject, and comparing the amount of metabolites to a reference value or a reference range.

In some embodiments, the methods described herein can be used to determine how long it will take for a subject having an early stage AMD to progress to an intermediate stage AMD or a late stage AMD, or how long it may take for a subject having an intermediate stage AMD to progress to a late stage AMD. In some cases, the methods include the steps of determining the amount of a group of appropriate metabolites in the sample from the subject, and comparing the amount of metabolites to a reference value or a reference range.

Metabolites

Metabolites are the intermediates and products of metabolism. They are usually small molecules (<1 kDa). Metabolites are the downstream product of the cumulative effects of the genome and its interaction with environmental exposures. Therefore, the metabolome can closely represent the "real functional state" of the biological system and therefore current disease phenotype.

The present disclosure provides lists of metabolites, which can be used to determine whether a subject has AMD, or the severity stage of AMD in the subject. These metabolites include all metabolites that are described in this disclosure, e.g., metabolites in Table 5, Table 6, Table 7, Table 8, and FIG. 3.

Table 5, Table 6, and Table 7 include the Odds Ratios (OR) for each metabolite. The reference term for Odds Ratios (OR) is the control group, which means that values lower than one represent a decrease in subjects with AMD as compared to controls (and the opposite for values higher than one). Thus, for the metabolites with an OR that is higher than 1, if the amount or level of metabolites in Table 5, Table 6, and Table 7 is higher than a reference value, the subject is more likely to have AMD; and if the amount or level of metabolites is less than the reference value, the subject is less likely to have AMD. On the other hand, for the metabolites with an OR that is lower than 1, if the amount of metabolites in Table 5, Table 6, and Table 7 is less than a reference value, the subject is more likely to have AMD; and if the amount of metabolites is more than the reference value, the subject is less likely to have AMD.

Figure 3:
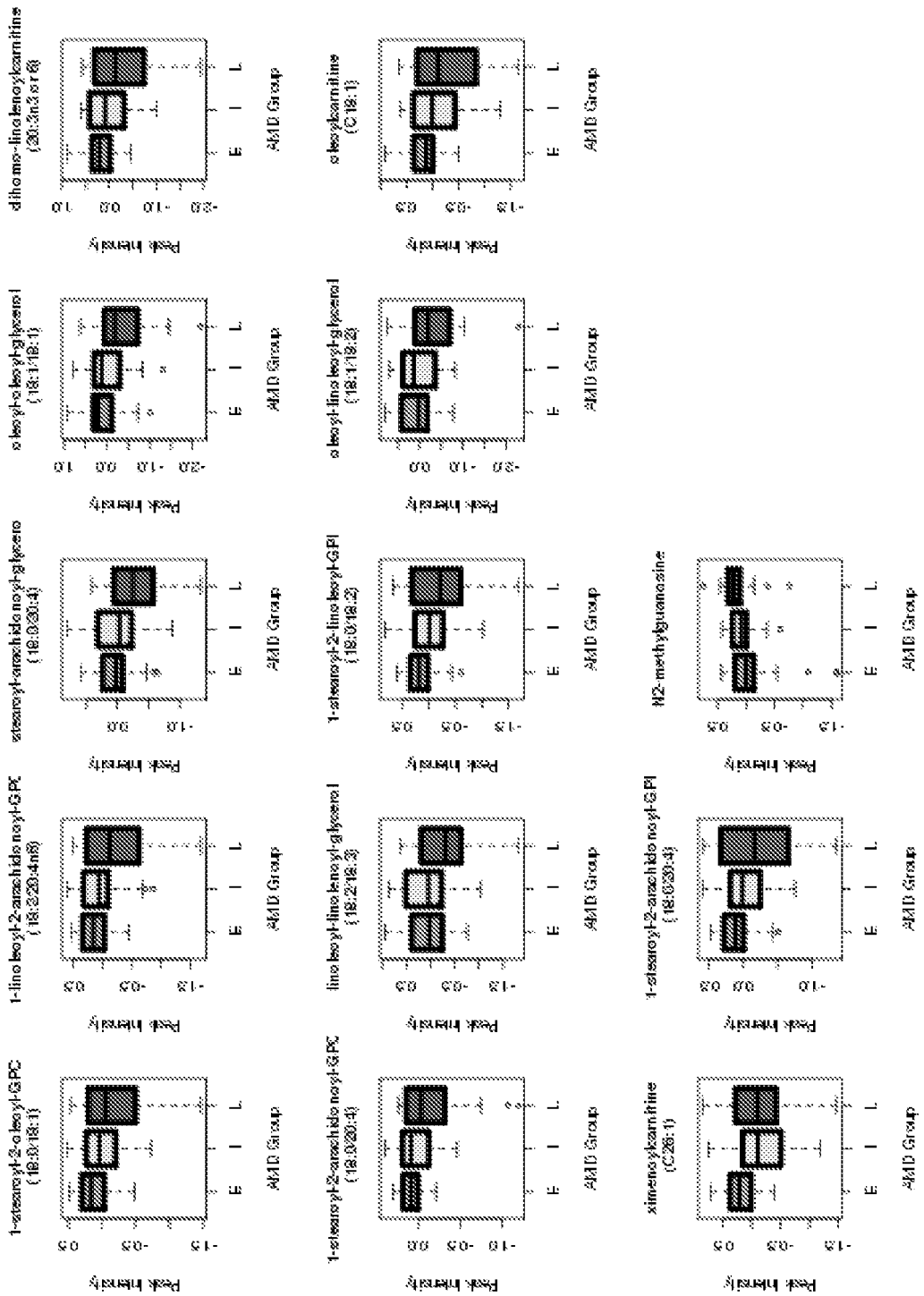
FIG. 3 is a set of boxplots of the 13 most significant metabolites (p<0.01) in an analysis of variance (ANOVA) study comparing severity stages of AMD (E—early; I—intermediate; L—late).

The metabolites as shown in Table 5, Table 6, Table 7, Table 8, and FIG. 3 can also be used to determine the stage of AMD. In some embodiments, an increased level of metabolites compared to levels found in healthy subjects or in subjects with early stage AMD is associated with more severe AMD. In some cases, two reference values are provided. For example, if the amount of metabolites is greater than a first reference value, the subject is likely to have late stage AMD. If the amount of metabolites is between the first reference value and the second reference value, the subject is likely to have intermediate stage AMD. And if the amount of metabolites is less than the second reference value, the subject is likely to have early stage AMD. In some cases, a third reference value is also provided. If the amount of metabolites is less than the third reference value, the subject is not likely to have an AMD. Some of these metabolites are shown in FIG. 3, e.g., N2-methylguanosine.

In some embodiments, a decreased level of metabolites is associated with more severe AMD. In some cases, two reference values are provided. For example, if the amount of metabolites is less than a first reference value, the subject is likely to have a late AMD. If the amount of metabolites is between the first reference value and the second reference value, the subject is likely to have an intermediate AMD. And if the amount of metabolites is more than the second reference value, the subject is likely to have an early AMD. In some cases, a third reference value is also provided. If the amount of metabolites is more than the third reference value, the subject is not likely to have an AMD. Some of these metabolites are shown in FIG. 3, e.g., 1-stearoyl-2-oleoyl-GPC, 1-linoleoyl-2-arachidonoyl-GPC, stearoyl-arachidonoyl-glycerol, oleoyl-oleoyl-glycerol, dihomo-linolenoylcarnitine, 1-stearoyl-2-arachidonoyl-GPC, linoleoyl-linolenoyl-glycerol, 1-stearoyl-2-linoleoyl-GPI, oleoylcarnitine, and 1-stearoyl-2-arachidonoyl-GPI.

In some embodiments, one or more reference ranges are provided. If the amount of metabolites is within a first reference range, the subject is not likely to have an AMD. If the amount of metabolites is within a second reference range, the subject is likely to have an early AMD. If the amount of metabolites is within a third reference range, the subject is likely to have an intermediate AMD. And if the amount of metabolites is within a fourth reference range, the subject is likely to have a late AMD.

The reference values and reference ranges used in the present methods can be determined empirically or by any means known in the art. In some embodiments, the reference values and reference ranges are determined by testing a large number of subjects, wherein the reference values or reference ranges can be selected for providing the highest accuracy, the highest positive predictive value, or the highest negative predictive value.

Mass Spectrometry

Mass spectrometry (MS) is an analytical technique that ionizes chemical species and sorts the ions based on their mass-to-charge ratio. It can be used to identify unknown compounds, determine the isotopic composition of elements in a molecule, and determine the structure of a compound by observing its fragmentation. MS has a high sensitivity and selectivity, which renders it increasingly popular in large scale metabolomics studies. Mass spectrometry is often used in tandem with chromatographic and other separation techniques (e.g., gas chromatography, liquid chromatography, and capillary electrophoresis). In some embodiments, Ultrahigh Performance Liquid Chromatography-Tandem MS/MS (UPLC-MS/MS) is used to analyze the metabolite profiles. The methods of analyzing metabolite profiles are described, e.g., in Mazzone P J, Wang X-F, Beukemann M, Zhang Q, Seeley M, Mohney R, et al. Metabolite Profiles of the Serum of Patients with Non-Small Cell Carcinoma. J Thorac Oncol. 2016 January; 11(1):72-8, which is incorporated herein by reference in its entirety.

Sample Collection

Samples for use in the methods described herein can include any of various types of biological fluids, cells, and/or tissues that can be isolated and/or derived from a subject. The sample can be collected from any fluid, cell, or tissue. In some embodiments, the sample is a fluid that is collected from eyes (e.g., aqueous humour, vitreous humour). In some embodiments, the sample is a postmortem sample (e.g., from postmortem eyes).

Samples can be obtained from a subject according to any methods known in the art. In some embodiments, the sample is, or is from, a biological fluid, e.g., blood (e.g., serum, plasma, or whole blood), semen, urine, saliva, tears, and/or cerebrospinal fluid, sweat, exosome or exosome-like microvesicles, lymph, ascites, bronchoalveolar lavage fluid, pleural effusion, seminal fluid, sputum, nipple aspirate, post-operative seroma or wound drainage fluid. In some embodiments, the sample is isolated and/or derived from peripheral blood or cord blood. In some embodiments, the sample is from a solid tissue, e.g., a biopsy sample, from skin, tumors, or lymph nodes. Biopsy samples can include, but are not limited to, resection biopsies, punch biopsy and fine-needle aspiration biopsy (FNA).

In some embodiments, the sample is a serum sample or a urine sample. The serum sample or the urine sample can have a volume of at least 1 mL (e.g., at least 2 mL, at least 3 mL, at least 4 mL, at least 5 mL, at least 6 mL, at least 7 mL, at least 8 mL, at least 9 mL, at least 10 mL, at least 12 mL, at least 14 mL, at least 16 mL, at least 18 mL, at least 20 mL, at least 22 mL, at least 24 mL, at least 26 mL, at least 28 mL, or at least 30 mL). For example, a serum sample or a urine sample can have a volume of between about 1 mL and about 5 mL, between about 5 mL and about 10 mL, between about 10 mL and about 20 mL, or between about 20 mL and about 30 mL.

In some examples of any of the methods described herein, the serum sample or the urine sample can be stored, e.g., for at least 1 hour (e.g., at least 6 hours, at least 12 hours, at least 1 day, at least 2 days, at least 3 days, at least 4 days, at least 5 days, at least 6 days, or at least 7 days) at a temperature below 25° C. (e.g., at about 15° C., at about 10° C., at about 4° C., at about 0° C., at about −20° C., at about −40° C., or at about −80° C.) prior to analyzing metabolites.

Principle Component Analysis

Principal component analysis (PCA) is a statistical method that uses an orthogonal transformation to convert a set of observations of possibly correlated variables into a set of values of linearly uncorrelated variables called principal components. It finds the principal components of the dataset and transforms the data into a new, lower-dimensional subspace.

The transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables.

Mathematically, the principal components are the eigenvectors of the covariance or correlation matrix of the original dataset. As the covariance matrix or correlation matrix is symmetric, the eigenvectors are orthogonal. The principal components (eigenvectors) correspond to the direction (in the original n-dimensional space) with the greatest variance in the data.

Each eigenvector has a corresponding eigenvalue. An eigenvalue is a scalar. The corresponding eigenvalue is a number that indicates how much variance there is in the data along that eigenvector (or principal component). A large eigenvalue means that that principal component explains a large amount of the variance in the data. Similarly, a principal component with a very small eigenvalue explains a small amount variance in the data.

To apply principle component analysis for the disclosed methods, a set of data consisting of multiple measurements (e.g., estimated amount of metabolites) is created for each sample. The set of data for a sample can be represented by a vector. For example, a vector X for Sample i can have the estimated amounts for "m" different metabolites. Thus, each vector is an m-dimensional vector, where m is the number of element. Each element can be a measurement. The elements in the vector can be the measurements of the same type (e.g., estimated amount of metabolites). They can be measurements of different types, e.g., including age, gender, and the estimated amount of metabolites. In some embodiments, the data that are used for principle component analysis include the amount of at least 5, at least 10, at least 20, at least 30, at least 40, at least 50, at least 60, at least 70, or at least 80 metabolites that are selected from Table 5, Table 6, Table 7, and/or Table 8.

In some embodiments, the data that are used for principle component analysis include the amount of one or more metabolites that are selected from Table 5 (e.g., all 7 metabolites in Table 5), one or more metabolites that are selected from Table 6 (e.g., all 87 metabolites in Table 6), one or more metabolites that are selected from Table 7 (e.g., all 33 metabolites in Table 7), or one or more metabolites that are selected from Table 8 (e.g., all 48 metabolites in Table 8).

In some examples, data are not normalized. In some examples, data are normalized. If the data are not normalized, attributes with large values and large variances (in absolute terms) will dominate the first principal component. In some cases, normalization can transform each attribute onto more or less to the same scale, so that each attribute has equal representation during principal component analysis.

The Principal Component Analysis generates principle components for the dataset. In some embodiments, 1, 2, 3, 4, 5, 6, 7, 8, 9, 10, 11, 12, 13, 14, 15, 16, 17, 18, 19, 20, or more than 20 principle components are generated. The first principal component captures the largest possible variance, and each succeeding component in turn explains the highest variance of the remaining variance. The Principal Component Analysis transforms the original dataset into a new, lower-dimensional subspace, and in this process, each subject is assigned to a value (coordinate) for each principle component (e.g., the first principle component, the second principle component, the first principle component, etc.). The corresponding value for each principle component can be further used in various analysis, e.g., regression analysis, and clustering analysis etc.

Detailed descriptions regarding how to perform PCA are described in numerous references, e.g., Smith, Lindsay I. "A tutorial on principal components analysis." Cornell University, USA 51 (2002): 52; and Shlens, Jonathon. "A tutorial on principal component analysis." arXiv preprint arXiv: 1404.1100 (2014), each of which is incorporated herein by reference in its entirety.

Clustering Analysis

Some embodiments of any of the methods described herein, further include clustering analysis. Clustering is a procedure to group samples in such a way that samples in the same group (called a cluster) are more similar to each other than to those in other groups (clusters). Clustering algorithms includes, but not limited to, hierarchical clustering algorithm, k-means clustering algorithm, a statistical distribution model, etc.

Hierarchical clustering is a method of cluster analysis which seeks to build a hierarchy of clusters. The basic process of hierarchical clustering is the following:

(1) Start by assigning each item to its own cluster, so that for N items, there will be N clusters. Each cluster initially contains just one item. Let the distances (similarities) between the clusters equal the distances (similarities) between the items they contain.

(2) Find the closest (most similar) pair of clusters and merge them into a single cluster.

(3) Compute distances (similarities) between the new cluster and each of the old clusters.

(4) Repeat steps 2 and 3 until all items are clustered into a single cluster of size N. A detailed description of clustering analysis can be found in numerous references, e.g., D'andrade, R. 1978, "U-Statistic Hierarchical Clustering" Psychometrika, 4:58-67; Johnson, S. C. 1967, "Hierarchical Clustering Schemes" Psychometrika, 2:241-254; Borgatti, Stephen P. "How to explain hierarchical clustering." (1994): 78-80, each of which is incorporated herein by reference in its entirety.

In some embodiments, k-means clustering can be used to analyze results of principle component analysis. K-means clustering aims to partition n observations into k clusters in which each observation belongs to the cluster with the nearest mean, serving as a prototype of the cluster. This results in a partitioning of the data space into Voronoi cells. In one example, the algorithm proceeds as follows:

(1) Choose k initial cluster centers (centroid), for example, choose k observations at random.

(2) Compute point-to-cluster-centroid distances of all observations to each centroid. There are many different ways to compute the distances, e.g., batch update, which assigns each observation to the cluster with the closest centroid; and online update, which individually assigns observations to a different centroid if the reassignment decreases the sum of the within-cluster, sum-of-squares point-to-cluster-centroid distances.

(3) Compute the average of the observations in each cluster to obtain k new centroid locations.

(4) Repeat steps 2 through 3 until cluster assignments do not change, or the maximum number of iterations is reached.

Detailed method of implementing K-means clustering is described, e.g., in U.S. Pat. No. 6,012,058, and in Kanungo et al. "An efficient k-means clustering algorithm: Analysis and implementation." IEEE transactions on pattern analysis and machine intelligence 24.7 (2002): 881-892, each of which is incorporated herein by reference in its entirety.

Furthermore, in some embodiments, clustering can be performed by a standard distribution model, e.g., multivariate normal distributions used by the expectation-maximization (EM) algorithm. The EM iteration alternates between performing an expectation (E) step, which creates a function for the expectation of the log-likelihood evaluated using the current estimate for the parameters, and a maximization (M) step, which computes parameters maximizing the expected log-likelihood found on the E step. These parameter-estimates are then used to determine the distribution of the latent variables in the next E step. Detailed methods of implementing EM algorithms are described in numerous references, e.g., in U.S. Pat. No. 6,615,205; PCT Application WO 2011162589; MacKay, David J C. Information theory, inference and learning algorithms. Cambridge University Press, 2003.

In some embodiments, the clustering analysis can place subjects with AMD and subjects without AMD into different groups. In some embodiments, the clustering analysis can place subjects with different stages of AMD into different groups. In some embodiments, if a test subject is grouped or associated with subjects with AMD, it can be determined that the test subject is likely to have AMD. In some embodiments, if a test subject is grouped or associated with subjects with a particular stage of AMD (e.g., early AMD), it can be determined that the test subject is likely to have this particular stage AMD.

Regression Analysis

Some embodiments of any of the methods described herein further include performing regression analysis on the data obtained from mass spectrometry or the data derived from mass spectrometry, e.g., results from principle component analysis.

In general, a linear regression equation is expressed as $$Y = \alpha + \beta_1 X_1 + \beta_2 X_2 + \ldots + \beta_k X_k + \varepsilon \qquad (I)$$

Y, the dependent variable, indicates a quantitative measure, e.g., a likelihood score that the subject has AMD, or the subject has a particular stage of AMD (e.g., early stage AMD), or a score indicating the seriousness of AMD (e.g., a score of 0 indicates that the subject does not have AMD, a score of 1 indicates that the subject has early stage AMD, a score of 2 indicates that the subject has intermediate stage AMD, and a score of 3 indicates that the subject has late stage AMD). The dependent variable Y depends on k explanatory variables (e.g., amounts of metabolites and/or results from principle component analysis), plus an error term that encompasses various unspecified omitted factors. In the above-identified model, the parameter $\beta_1$ gauges the effect of the first explanatory variable $X_1$ on the dependent variable Y. $\beta_2$ gives the effect of the explanatory variable $X_2$ on Y. It will also be appreciated by those of skill in the art that a is a constant, and c is an error term.

A logistic regression model is a non-linear transformation of the linear regression. The logistic regression model is often referred to as the "logit" model and can be expressed as $$\ln[p/(1-p)] = \alpha + \beta_1 X_1 + \beta_2 X_2 + \ldots + \beta_k X_k + \varepsilon \qquad (II)$$

where,

α is a constant, and ε is an error term, ln is the natural logarithm, $\log_{(e)}$, where e=2.71828 . . . , p is the probability that the event Y occurs, p/(1−p) is the "odds", ln [p/(1−p)] is the log odds, or "logit."

It will be appreciated by those of skill in the art that a and c can be folded into a single constant, and expressed as a. In some embodiments, a single term α is used, and ε is omitted. The "logistic" distribution is an S-shaped distribution function. The logit distribution constrains the estimated probabilities (p) to lie between 0 and 1.

In some embodiments, the logistic regression model is expressed as $$Y = \alpha + \Sigma \beta_i X_i \quad (III)$$

Here, Y is a value indicating whether a test sample classifies with a group of subjects, e.g., whether the test subject classifies with a group of subjects having AMD, as opposed to a group of subjects not having AMD; or whether the test subject classifies with a group of subjects having a particular stage of AMD, as opposed to subjects without AMD or with a different stage of AMD.

The probability that a test sample classifies with a particular group of subjects, as opposed to the other groups, can be derived from Y. The higher the score, the higher the probability that the test sample classifies with the group of interest. $X_i$ is an explanatory variable. In some embodiments, $X_i$ can be results obtained from principle component analysis, e.g., $X_1$ can be the value (coordinate) for the first principle component, $X_2$ can be the value (coordinate) for the second principle component, $X_3$ can be the value (coordinate) for the third principle component. In some embodiments, Xi indicate the amount of metabolites in a sample, and the data can be obtained from mass spectrometry.

In some embodiments, the logistic regression model is fit by maximum likelihood estimation (MLE). The coefficients (e.g., $\alpha$, $\beta_1$, $\beta_2$, . . . ) are determined by maximum likelihood. A likelihood is a conditional probability (e.g., P(Y|X), the probability of Y given X). The likelihood function (L) measures the probability of observing the particular set of dependent variable values ($Y_1, Y_2, \ldots, Y_n$) that occur in the sample data set. In some embodiments, it is written as the product of the probability of observing Y1, $Y_2, \ldots, Y_n$:

$$L = \text{Prob}(Y_1, Y_2, \ldots, Y_n) = \text{Prob}(Y_1) * \text{Prob}(Y_2) * \ldots \text{Prob}(Y_n) \quad (IV)$$

The higher the likelihood function, the higher the probability of observing the Ys in the sample. MLE involves finding the coefficients ($\alpha$, $\beta_1$, $\beta_2$, . . . ) that make the log of the likelihood function (LL<0) as large as possible or −2 times the log of the likelihood function (−2LL) as small as possible. In MLE, some initial estimates of the parameters $\alpha$, $\beta_1$, $\beta_2$, and so forth are made. Then, the likelihood of the data given these parameter estimates is computed. The parameter estimates are improved, the likelihood of the data is recalculated. This process is repeated until the parameter estimates remain substantially unchanged (for example, a change of less than 0.01 or 0.001). Examples of logistic regression and fitting logistic regression models are found in Hastie, The Elements of Statistical Learning, Springer, N.Y., 2001, pp. 95-100.

Once the logistic regression equation coefficients and the logistic regression equation constant are determined, the model can be readily applied to a test subject to obtain Y. In one embodiment, Y can be used to calculate probability (p) by solving the function $Y = \ln(p/(1-p))$.

Analysis System and Computer Implementation

In some embodiments, analysis as disclosed in the present disclosure can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible program carrier for execution by, or to control the operation of, a processing device. Alternatively, or in addition, the program instructions can be encoded on a propagated signal that is an artificially generated signal, e.g., a machine-generated electrical, optical, or electromagnetic signal that is generated to encode information for transmission to suitable receiver apparatus for execution by a processing device. A machine-readable medium can be a machine-readable storage device, a machine-readable storage substrate, a random or serial access memory device, or a combination of one or more of them.

In some embodiments, analysis methods as disclosed in the present disclosure are implemented in the form of computer program instructions and executed by processing device. Suitable programming languages for expressing the program instructions include, but are not limited to, C, C++, Java, Python, SQL, Perl, Tcl/Tk, JavaScript, ADA, OCaml, Haskell, Scala, and statistical analysis software, such as SAS, R, MATLAB, SPSS, COREexpress® statistical analysis software and Stata etc. Various aspects of the methods may be written in different computing languages from one another, and the various aspects are caused to communicate with one another by appropriate system-level-tools available on a given system.

The processes and logic flows described in this specification can be performed by one or more programmable computers executing one or more computer programs to perform functions by operating on input information and generating output. The processes and logic flows can also be performed by, and apparatus can also be implemented as, special purpose logic circuitry, e.g., an FPGA (field programmable gate array) or an ASIC (application specific integrated circuit) or RISC.

Computers suitable for the execution of a computer program include, by way of example, general or special purpose microprocessors or both, or any other kind of central processing unit. Generally, a central processing unit will receive instructions and information from a read only memory or a random access memory or both. The essential elements of a computer are a central processing unit for performing or executing instructions and one or more memory devices for storing instructions and information. Generally, a computer will also include, or be operatively coupled to receive information from or transfer information to, or both, one or more mass storage devices for storing information, e.g., magnetic, magneto optical disks, or optical disks.

Computer readable media suitable for storing computer program instructions and information include various forms of non-volatile, tangible memory, media and memory devices, including by way of example semiconductor memory devices, e.g., EPROM, EEPROM, and flash memory devices; magnetic disks, e.g., internal hard disks or removable disks; magneto optical disks; and CD ROM and (Blue Ray) DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back end component, e.g., as an information server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital information communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, the server can be in the cloud via cloud computing services.

While this specification includes many specific implementation details, these should not be construed as limitations on the scope of any of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

EXAMPLES

The invention is further described in the following examples, which do not limit the scope of the invention described in the claims.

Example 1: Human Plasma Metabolomics Study Across all Stages of Age-Related Macular Degeneration Identifies Potential Lipid Biomarkers Experiments and analyses were performed to characterize the plasma metabolomics profile of patients with age-related macular degeneration (AMD), using mass-spectrometry (MS).
Methods
Study Design This study was part of a cross-sectional, observational study on AMD biomarkers. The research protocol was conducted in accordance with HIPAA (Health Insurance Portability and Accountability Act) requirements and the tenets of the Declaration of Helsinki, and was approved by the Institutional Review Board (IRB). All included participants provided written informed consent and were prospectively recruited.

Study Protocol

Subjects with a diagnosis of AMD at the time of their regular appointments were recruited. Exclusion criteria included diagnosis of any other vitreoretinal disease, active uveitis or ocular infection, significant media opacities that precluded the observation of the ocular fundus, refractive error equal or greater than 6 diopters of spherical equivalent, past history of retinal surgery, history of any ocular surgery or intra-ocular procedure (such as laser and intra-ocular injections) within the 90 days prior to enrollment, and diagnosis of diabetes mellitus, with or without concomitant diabetic retinopathy. Additionally, a control group of subjects aged 50 years or older, without any evidence of AMD in either eye, was identified and consented for the study. The same exclusion criteria were applied.

All participants underwent a comprehensive eye exam, including best-corrected visual acuity (BCVA), current refraction, intra-ocular pressure, slit lamp bio-microscopy, and dilated fundus exam. A standardized medical history questionnaire was designed specifically for this study, including, among others, self-reported data on smoking habits (smokers were considered those who reported current smoking and ex-smokers those who have ever smoked, regardless of when they stopped, but who do not currently smoke), and weight and height, which were used to calculate body mass index. If the study participants did not know their current height and/or weight, these were obtained by a study investigator.

Non-stereoscopic, 7 field, color fundus photographs (CFP) (Topcon TRC-50DX, Topcon Corporation, Tokyo, Japan; or Zeiss FF-450Plus, Carl Zeiss Meditec, Dublin, Calif.) were obtained at the same visit. These were used for AMD diagnosis and grading, according to the AREDS classification system. Two independent experienced graders analyzed all field 2 CFP on IMAGEnet 2000 software (version 2.56; Topcon Medical Systems). In cases of disagreement, a senior author (DH) established the final categorization. All graders were masked to the patients' clinical and demographic characteristics during this process.

The most recent AREDS2 definitions were adopted, namely that the standard disc diameter equals 1800 μm (rather than 1500 μm), which affects the size of the Early Treatment Diabetic Retinopathy Study (ETDRS) grid and of the standard drusen circles; and that geographic atrophy (GA) is present if the lesion has a diameter equal or greater than 433 μm (AREDS circle 1-2) and has at least two of the following features—absence of RPE pigment, circular shape, or sharp margins (foveal involvement not a requirement). With these criteria, the following groups were established: controls (AREDS stage 1)—presence of drusen maximum size<circle C0 and total area<C1; early AMD (AREDS stage 2)—drusen maximum size≥C0 but <C1 or presence of AMD characteristic pigment abnormalities in the inner or central subfields; intermediate AMD (AREDS stage 3)—presence drusen maximum size≥C1 or of drusen maximum size≥C0 if the total area occupied was >I2 for soft indistinct drusen and >O2 for soft distinct drusen; late AMD (AREDS stage 4)—presence of GA according to the criteria described above or evidence of neovascular AMD. For subjects with different severity stages in the two eyes (example: early AMD in one eye and intermediate in the other eye), the more advanced stage was assumed.
Sample Collection and Mass Spectrometry Analysis The present study used a single plasma collection per individual. For all participants, after confirmed fasting, blood samples were collected into sodium-heparin tubes, and centrifuged within 30 min (1500 rpm, 10 min, 20° C.).

Plasma aliquots of 1.5 mL were transferred into sterile cryovials and stored at −80° C. When all subjects had been recruited, plasma samples were shipped to a facility for analysis in dry ice (through TNT® Express, USA, INC). Samples arrived frozen in less than 24 hours and were immediately stored at −80° C. until processing.

Sample Processing

Frozen serum aliquots were thawed, and processed using an automated MicroLab STAR® system (Hamilton, Reno, Nev.), using a series of organic and aqueous extractions to remove the protein fraction in sera while allowing maximum recovery of small molecules. Recovery standards were added prior to the first step in the extraction process for quality control (QC) purposes. The resulting extract was divided into five fractions: two for analysis by two separate reverse phase (RP) Ultrahigh Performance Liquid Chromatography (UPLC)-MS/MS methods with positive ion mode electrospray ionization (ESI); one for analysis by RP/UPLC-MS/MS with negative ion mode ESI; one for analysis by HILIC/UPLC-MS/MS with negative ion mode ESI; and one sample was reserved for backup. Samples were placed briefly on a TurboVap® (Zymark) to remove the organic solvent. The sample extracts were stored overnight under nitrogen before preparation for analysis.

Mass Spectrometry Analysis

Non-targeted MS analysis was performed using Ultrahigh Performance Liquid Chromatography-Tandem MS (UPLC-MS/MS). The protocols were described in Mazzone P J, Wang X-F, Beukemann M, et al. Metabolite Profiles of the Serum of Patients with Non-Small Cell Carcinoma. J Thorac Oncol. 2016; 11(1):72-78. doi:10.1016/j.jtho.2015.09.002, which is incorporated by reference in its entirety. Briefly, plasma samples were analyzed with a Waters ACQUITY ultra-UPLC and a Thermo Scientific Q-Exactive high resolution/accurate mass spectrometer, interfaced with a heated electrospray ionization (HESI-II) source and Orbitrap mass analyzer operated at 35,000 mass resolution. The sample extracts were dried then reconstituted in solvents compatible to each of the four methods applied: acidic positive ion conditions, chromatographically optimized for more hydrophilic compounds; acidic positive ion conditions, but chromatographically optimized for more hydrophobic compounds (for both, extracts were gradient eluted from a C18 column using water, methanol, perfluoropentanoic acid and formic acid); basic negative ion optimized conditions, using a separate dedicated C18 column; and negative ionization following elution from a HILIC column (using a gradient of water and acetonitrile with ammonium formate, pH 10.8). The MS analysis alternated between MS and data-dependent MS scans using dynamic exclusion. The scan range varied slighted between methods but covered 70-1000 m/z.

Raw data was extracted, peak-identified and QC processed. Compounds were identified by comparison to library entries of purified standards or recurrent unknown entities. A library was established based on authenticated standards that contains the retention time/index (RI), mass to charge ratio (m/z), and chromatographic data (including MS/MS spectral data) on all molecules present in the library. Furthermore, biochemical identifications are based on three criteria: retention index within a narrow RI window of the proposed identification, accurate mass match to the library+/−10 ppm, and the MS/MS forward and reverse scores between the experimental data and authentic standards. The MS/MS scores are based on a comparison of the ions present in the experimental spectrum to the ions present in the library spectrum. While there may be similarities between these molecules based on one of these factors, the use of all three data points can be utilized to distinguish and differentiate biochemicals. More than 3300 commercially available purified standard compounds have been acquired and registered for analysis on all platforms for determination of their analytical characteristics. Additional mass spectral entries have been created for structurally unnamed biochemicals, which have been identified by virtue of their recurrent nature (both chromatographic and mass spectral). Peaks were quantified using area-under-the-curve.

Statistical and Data Analysis

Traditional descriptive methods were used to describe the clinical and demographic characteristics of the included study population—mean and standard deviation for continuous variables, and percentages for dichotomous/categorical variables. The four study groups were compared using ANOVA and Chi-square tests.

Figure 4:
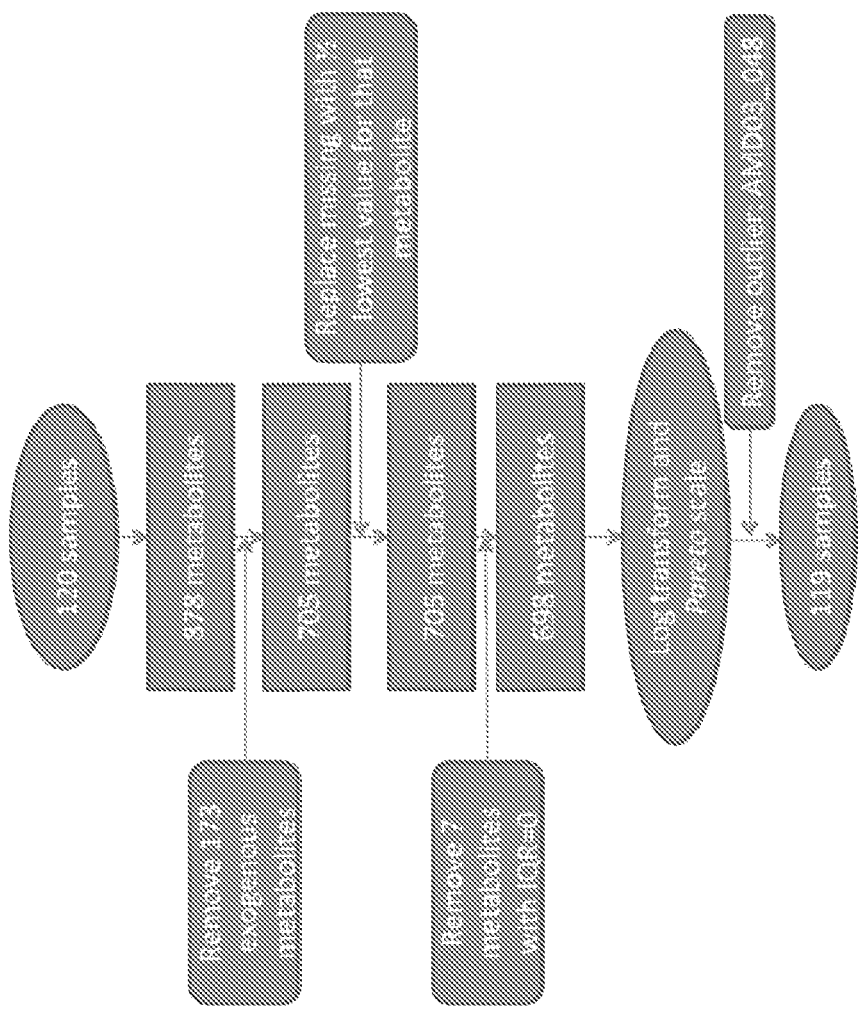
FIG. 4 is a flow-chart showing the analyzed samples and metabolites in Example 1.
Figure 5C:
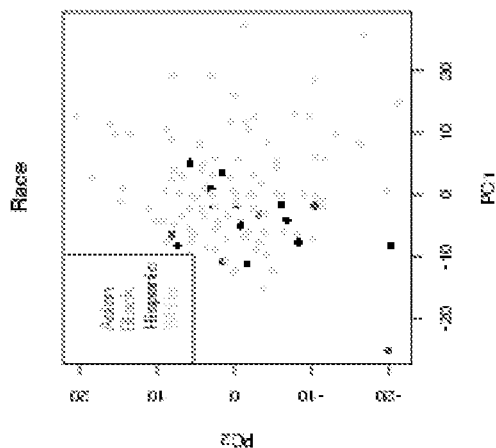
FIGS. 5A-5E is a set of scatter plots of PC1 and PC2 with each subject being labeled based on age, gender, race, body mass index (BMI) or smoking status.
Figure 5B:
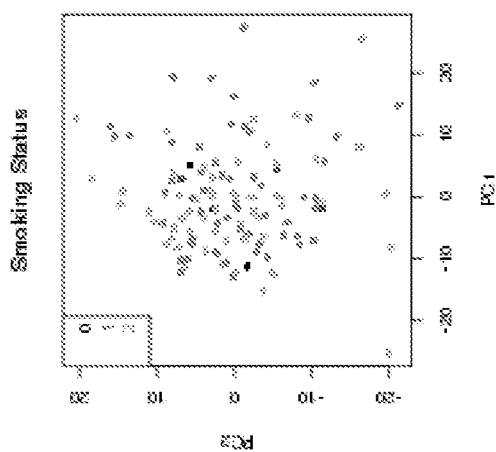
Figure 5A:
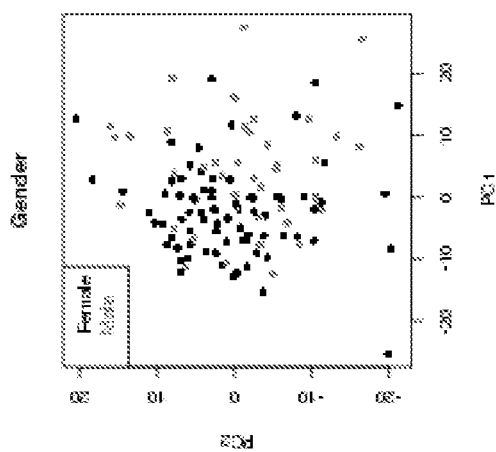
Figures 5D, 5E:
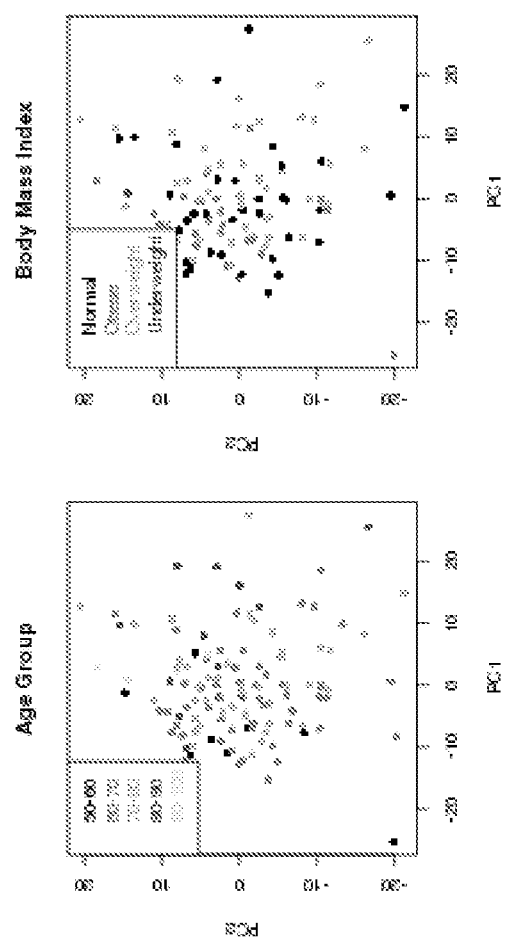

In this dataset, 878 named metabolites were identified, of which 384 (44%) mapped to the lipid pathways. One hundred and seventy-three metabolites determined to be exogenous to humans (including medications, food additives and buffering agents) were excluded from analysis. One subject (a male with early AMD) who had missing or undetectable levels for >30% of metabolites was excluded. Any missing values for the remaining subjects were imputed with half the minimum detected level for that metabolite. To ensure only the most informative metabolites were included in the analysis, those metabolites with an interquartile range of zero were excluded. This left 698 metabolites that were pareto scaled and log-transformed for analysis. FIG. 4 presents the included metabolites and samples.

Initial principal component analysis (PCA) was performed to assess if clustering could be identified between AMD (and its severity stages) and controls. Regression models were constructed to determine an association between AMD stage, potential confounders and the principal components.

To identify the metabolites significantly associated with AMD as compared to normal macular health, a multivariate logistic regression was performed adjusting for age, gender, BMI and smoking status. The discriminatory ability of the significant metabolites was assessed using a summary score based on their first principal component and receiver operator curve (ROC) analyses. The significant metabolites were further assessed to see if they were able to discriminate between early, intermediate and late AMD cases using ANOVA.

Metabolite set enrichment analysis using Metaboanalyst 3.0 was performed on the significant metabolites to interpret these findings biologically.

Results

Study Population 120 subjects were recruited, 25% (n=30) with normal macular health (control group) and 75% (n=90) with AMD. One patient with AMD (early AMD) was considered an outlier, and thus excluded from further analyses. Table 1 presents the clinical and demographic characteristics of the study group. Among the potential confounders evaluated, only age presented a statistically significant difference among the different study groups (p=0.0005) (Table 1).

TABLE 1

Clinical and demographic characteristics of the study population

| | | Total Population (n = 119) | Control (n = 30) | Early (n = 29) | Intermediate (n = 30) | Late (n = 30) | p-value |
|---|---|---|---|---|---|---|---|
| Age in years | (mean[SD]) | 70 [8] | 68 [10] | 68 [7] | 70 [5] | 76 [8] | 0.0005* |
| Gender | (n male[%]) | 43 [36%] | 12 [40%] | 9 [31%] | 9 [30%] | 13 [43%] | 0.640 |
| BMI | (mean[SD]) | 27 [5] | 26 [4] | 27 [5] | 29 [7] | 27 [4] | 0.070 |
| Ethnicity | (n white[%]) | 101 [85%] | 22 [73%] | 24 [83%] | 30 [100%] | 25 [83%] | 0.176 |
| | (n black/hispanic/asian [%]) | 7 [6%] | 2 [7%] | 3 [10%] | 0 | 2 [7%] | |
| | (n unknown [%]) | 11 [9%] | 6 [20%] | 2 [7%] | 0 | 3 [10%] | |
| Smoking | (n Non-smoker [%]) | 57 [48%] | 18 [60%] | 18 [62%] | 13 [43%] | 8 [27%] | 0.057 |
| | (n Ex-smoker [%]) | 56 [47%] | 10 [33%] | 11 [38%] | 15 [50%] | 20 [67%] | |
| | (n Smoker [%]) | 3 [3%] | 1 [3%] | 0 | 2 [7%] | 0 | |
| | (n NA [%]) | 3 [3%] | 1 [3%] | 0 | 0 | 2 [7%] | |
| Age started smoking in yrs | (mean [SD]) | 19 [7] | 20 [7] | 16 [4] | 22 [10] | 17 [4] | 0.055 |
| Age stopped smoking in yrs | (mean [SD]) | 39 [13] | 37 [11] | 34 [16] | 42 [12] | 42 [13] | 0.315 |
| N cigarettes per day | (mean [SD]) | 18 [14] | 18 [10] | 9 [8] | 20 [18] | 20 [14] | 0.244 |
| AMD subtype | (n Choroidal Neovascularization; Wet [%]) | 25 [28] | n/a | n/a | n/a | 25 [83] | $1.8 \times 10^{-17}$ |
| | (n Geographic Atrophy; dry [%]) | 4 [5] | n/a | n/a | n/a | 4 [13] | |

Legend: AMD—Age-related Macular degeneration; SD—standard deviation; n—number. Significant differences (p < 0.05) are marked as *, and represent the result of ANOVA for continuous variables and Chi-square test for dichotomous variables.

Principal Component Analysis

The scores plot of the first two principal components (PC1 and PC2), which accounted for 20% of the variance in the data, is presented in FIG. 1. In the figure, PC1 indicates the first principal component, PC2 indicates the second principal component. As shown, there is some evidence for a shift between the late stage cases (blue) as compared to the controls (black). The first ten PCs cumulatively explained 50% of the variance in the data. When all ten PCs were included in one model, regression analysis indicated that three of these ten PCs (PC2, PC8 and PC9) were significantly associated with AMD (Table 2).

TABLE 2

Association between the ten first principal components and AMD

| PC | Cumulative % of variance explained | β coefficient | 95% CI | p-value |
|---|---|---|---|---|
| PC1 | 10.6% | 0.06 | 0; 0.13 | 0.070 |
| PC2 | 20.1% | −0.10 | 0.17; −0.03 | 0.007* |
| PC3 | 26.9% | −0.04 | −0.12; 0.03 | 0.287 |
| PC4 | 32.0% | 0.07 | −0.01; 0.15 | 0.089 |
| PC5 | 36.1% | 0.02 | −0.08; 0.11 | 0.744 |
| PC6 | 39.5% | −0.02 | −0.13; 0.08 | 0.690 |
| PC7 | 42.5% | −0.02 | −0.14; 0.10 | 0.736 |
| PC8 | 44.9% | −0.14 | −0.29; −0.02 | 0.031* |
| PC9 | 47.3% | −0.18 | −0.32; −0.05 | 0.010* |
| PC10 | 49.5% | 0.11 | −0.03; 0.25 | 0.133 |

Legend: PC—principal component; CI—confidence interval. Significant p-values are marked as *.

When the association between the PCs and the potential confounders was assessed, PC2 and PC8 were additionally associated with age, while PC9 was also associated with BMI (Table 3 and FIGS. 5A-5E). When a regression model adjusting for age (PC2 and PC8) or BMI (PC9) was run, PC2 and PC9 retained significance (P<0.05), suggesting that PC8 can in fact be driven by metabolites relating to age. Pathway enrichment analyses of the metabolites with the highest loadings for PC2 and PC9 (<−0.1 or >0.1) determined that these metabolites were enriched for fatty acid biosynthesis ($p=3.8 \times 10^{-4}$), linoleic acid metabolism ($p=8.7 \times 10^{-4}$) (PC2), sphingolipid metabolism ($p=6.5 \times 10^{-8}$), glycerophospholipid metabolism ($p=3.3 \times 10^{-4}$) and purine metabolism ($p=5.4 \times 10^{-4}$) (PC9).

TABLE 3

Principal component analysis by confounders

| | Age | | | Gender | | | BMI | | | Smoking status | | |
|---|---|---|---|---|---|---|---|---|---|---|---|---|
| | Estimate | 95% CI | p-value | Estimate | 95% CI | p-value | Estimate | 95% CI | p-value | Estimate | 95% CI | p-value |
| PC1 | 0.39 | 0.26, 0.53 | <0.0001* | 1.29 | 1.15, 1.53 | 0.0003* | −0.1 | 0.19, 0 | 0.0593 | 0.01 | 0, 0.02 | 0.0986 |
| PC2 | 0.19 | 0.05, 0.33 | 0.0093* | 0.97 | 0.85, 1.09 | 0.5848 | 0.02 | −0.09, 0.12 | 0.7677 | 0 | −0.02, 0.01 | 0.617 |
| PC3 | 0.08 | −0.09, 0.24 | 0.3754 | 1.51 | 1.27, 1.98 | 0.0002* | 0.17 | 0.04, 0.29 | 0.0097* | 0 | −0.01, 0.02 | 0.5432 |
| PC4 | 0.52 | 0.33, 0.71 | <0.0001* | 0.97 | 0.84, 1.11 | 0.6293 | −0.15 | −0.3, 0 | 0.0527 | −0.01 | −0.02, 0.01 | 0.452 |
| PC5 | 0.26 | 0.05, 0.48 | 0.0175* | 0.57 | 0.39, 0.72 | 0.0002* | 0.24 | 0.07, 0.41 | 0.0066* | 0 | −0.02, 0.02 | 0.8483 |
| PC6 | 0.14 | −0.09, 0.38 | 0.2426 | 0.89 | 0.75, 1.03 | 0.1405 | −0.27 | −0.45, −0.1 | 0.0032* | 0 | −0.02, 0.02 | 0.9893 |
| PC7 | 0.06 | −0.19, 0.32 | 0.6375 | 1.13 | 0.92, 1.42 | 0.2623 | −0.05 | −0.23, 0.14 | 0.631 | 0.01 | −0.02, 0.03 | 0.6464 |

TABLE 3-continued

Principal component analysis by confounders

| | Age | | | Gender | | | BMI | | | Smoking status | | |
|---|---|---|---|---|---|---|---|---|---|---|---|---|
| | Estimate | 95% CI | p-value | Estimate | 95% CI | p-value | Estimate | 95% CI | p-value | Estimate | 95% CI | p-value |
| PC8 | −0.5 | −0.78, −0.23 | 0.0005* | 0.84 | 0.67, 1.04 | 0.1227 | 0.18 | −0.03, 0.4 | 0.0994 | 0.01 | −0.01, 0.04 | 0.3448 |
| PC9 | 0.17 | −0.12, 0.45 | 0.2479 | 1.6 | 1.23, 2.34 | 0.0032* | −0.28 | −0.49, −0.06 | 0.0141* | −0.02 | −0.04, 0.01 | 0.2116 |
| PC10 | 0.25 | −0.04, 0.54 | 0.0957 | 0.76 | 0.53, 1.01 | 0.0984 | −0.3 | −0.53, −0.08 | 0.0091* | 0.01 | −0.01, 0.04 | 0.3857 |

Legend: PC—principal component; CI—confidence interval; BMI—body mass index. P-values < 0.05 are marked as *.

Multivariate Logistic Regression Analysis

For multivariate analyses, a dichotomous outcome was used: normal macular health (controls, n=30) versus AMD (n=89) (Table 4). The results revealed that, after controlling for age, gender, BMI and smoking status, 87 metabolites were associated with AMD (P<0.05) (Table 6), and 33 metabolites were associated with AMD (P<0.01) (Table 7). Most of these metabolites (82.8%, n=72) belonged to the lipid super-pathway, followed by amino acids (5.7%, n=5; including N-acetylasparagine, a component of alanine and aspartate metabolism). The remaining were peptides (4.6%, n=4), cofactors, and vitamins (2.3%, n=2), and metabolites involved in purine and pyrimidine metabolism (4.6%, n=4). Of the seven most significant metabolites (p<0.001, Table 5), all but one (adenosine) were lipids (4 diacylglycerols, and 2 phosphatidylcholines).

TABLE 4

Multivariate logistic regression analysis considering AMD vs controls

| | | Metabolites as compared to controls | | | | | |
|---|---|---|---|---|---|---|---|
| | | Decreased in AMD patients (OR < 1) | | Increased in AMD patients (OR > 1) | | Total | |
| | | Number | % | Number | % | Number | % |
| Significance level | p < 0.05 | 59 | 8.5% | 28 | 4.0% | 87 | 12.5% |
| | p < 0.01 | 24 | 3.4% | 9 | 1.3% | 33 | 4.7% |
| | p < 0.001 | 6 | 0.9% | 1 | 0.1% | 7 | 1.0% |

Legend: AMD—age-related macular degeneration; OR—Odds ratio.

TABLE 5

Significantly different metabolites (p < 0.001) between patients with AMD and controls

| Biochemical | Super-pathway | Sub-pathway | AMD patients vs controls | Odds ratio | P-value |
|---|---|---|---|---|---|
| linoleoyl-arachidonoyl-glycerol (18:2/20:4) | Lipid | Diacylglycerol | Decreased | 0.0961 | 0.0008 |
| stearoyl-arachidonoyl-glycerol (18:0/20:4) | Lipid | Diacylglycerol | Decreased | 0.0411 | 0.0009 |
| oleoyl-arachidonoyl-glycerol (18:1/20:4) | Lipid | Diacylglycerol | Decreased | 0.0463 | 0.0002 |
| oleoyl-arachidonoyl-glycerol (18:1/20:4) | Lipid | Diacylglycerol | Decreased | 0.111 | 0.0007 |
| 1-palmitoyl-2-arachidonoyl-GPC (16:0/20:4n6) | Lipid | Phosphatidylcholine (PC) | Decreased | 0.0004 | 0.0006 |
| 1-stearoyl-2-arachidonoyl-GPC (18:0/20:4) | Lipid | Phosphatidylcholine (PC) | Decreased | 0.0002 | 0.0005 |
| adenosine | Nucleotide | Purine Metabolism, Adenine containing | Increased | 3.7422 | 0.0009 |

Legend: The reference term for Odds Ratios (OR) is the control group, which means that values lower than one represent a decrease in subjects with AMD as compared to controls (and the opposite for values higher than one).

TABLE 6

87 significantly different metabolites (p < 0.05) between patients with AMD and controls

| Metabolites | SUPER_PATHWAY | SUB_PATHWAY | Odds Ratio (OR) | P value |
|---|---|---|---|---|
| adenosine 5'-monophosphate (AMP) | Nucleotide | Purine Metabolism, Adenine containing | 3.271218 | 0.003173 |

TABLE 6-continued 87 significantly different metabolites (p < 0.05) between patients with AMD and controls

| Metabolites | SUPER_PATHWAY | SUB_PATHWAY | Odds Ratio (OR) | P value |
|---|---|---|---|---|
| adenosine | Nucleotide | Purine Metabolism, Adenine containing | 3.742296 | 0.000913 |
| glycerophosphoethanolamine | Lipid | Phospholipid Metabolism | 6.524345 | 0.039145 |
| glycerol 3-phosphate | Lipid | Glycerolipid Metabolism | 6.065232 | 0.049842 |
| palmitoylcarnitine (C16) | Lipid | Fatty Acid Metabolism(Acyl Carnitine) | 0.131938 | 0.012468 |
| phosphoethanolamine | Lipid | Phospholipid Metabolism | 3.604797 | 0.018942 |
| 1,2-dipalmitoyl-GPC (16:0/16:0) | Lipid | Phosphatidylcholine (PC) | 0.031428 | 0.012878 |
| malonate | Lipid | Fatty Acid Synthesis | 0.17224 | 0.045065 |
| isovalerate | Amino Acid | Leucine, Isoleucine and Valine Metabolism | 4.152345 | 0.034145 |
| cysteine s-sulfate | Amino Acid | Methionine, Cysteine, SAM and Taurine Metabolism | 0.153389 | 0.003077 |
| N-carbamoylaspartate | Nucleotide | Pyrimidine Metabolism, Orotate containing | 2.576912 | 0.047215 |
| stearoylcarnitine (C18) | Lipid | Fatty Acid Metabolism(Acyl Carnitine) | 0.160933 | 0.006154 |
| biliverdin | Cofactors and Vitamins | Hemoglobin and Porphyrin Metabolism | 7.503205 | 0.009436 |
| alpha-tocopherol | Cofactors and Vitamins | Tocopherol Metabolism | 11.84447 | 0.009147 |
| laurylcarnitine (C12) | Lipid | Fatty Acid Metabolism(Acyl Carnitine) | 0.299141 | 0.021326 |
| N-acetyl-cadaverine | Amino Acid | Lysine Metabolism | 2.474719 | 0.040485 |
| oleoylcarnitine (C18:1) | Lipid | Fatty Acid Metabolism(Acyl Carnitine) | 0.192606 | 0.020323 |
| myristoylcarnitine (C14) | Lipid | Fatty Acid Metabolism(Acyl Carnitine) | 0.228735 | 0.014033 |
| 1-palmitoyl-2-oleoyl-GPE (16:0/18:1) | Lipid | Phosphatidylethanolamine (PE) | 0.255716 | 0.021705 |
| 1-palmitoyl-2-arachidonoyl-GPE (16:0/20:4) | Lipid | Phosphatidylethanolamine (PE) | 0.169948 | 0.009794 |
| N2-methylguanosine | Nucleotide | Purine Metabolism, Guanine containing | 2.94784 | 0.038961 |
| N-acetylasparagine | Amino Acid | Alanine and Aspartate Metabolism | 5.772255 | 0.048318 |
| 12-HETE | Lipid | Eicosanoid | 0.265821 | 0.026979 |
| margaroylcarnitine | Lipid | Fatty Acid Metabolism(Acyl Carnitine) | 0.18284 | 0.012731 |
| cerotoylcarnitine (C26) | Lipid | Fatty Acid Metabolism(Acyl Carnitine) | 0.149148 | 0.012331 |
| palmitoyl-oleoyl-glycerol (16:0/18:1) | Lipid | Diacylglycerol | 0.210667 | 0.010585 |
| palmitoyl-linoleoyl-glycerol (16:0/18:2) | Lipid | Diacylglycerol | 0.27047 | 0.009372 |
| palmitoyl-arachidonoyl-glycerol (16:0/20:4) | Lipid | Diacylglycerol | 0.192538 | 0.003875 |
| palmitoyl-arachidonoyl-glycerol (16:0/20:4) | Lipid | Diacylglycerol | 0.252937 | 0.0071 |
| palmitoleoyl-linoleoyl-glycerol (16:1/18:2) | Lipid | Diacylglycerol | 0.250453 | 0.009831 |
| oleoyl-oleoyl-glycerol (18:1/18:1) | Lipid | Diacylglycerol | 0.203597 | 0.01594 |
| oleoyl-oleoyl-glycerol (18:1/18:1) | Lipid | Diacylglycerol | 0.344558 | 0.036502 |
| oleoyl-linoleoyl-glycerol (18:1/18:2) | Lipid | Diacylglycerol | 0.262443 | 0.016373 |
| oleoyl-linoleoyl-glycerol (18:1/18:2) | Lipid | Diacylglycerol | 0.250893 | 0.027595 |
| oleoyl-arachidonoyl-glycerol (18:1/20:4) | Lipid | Diacylglycerol | 0.046336 | 0.000159 |
| oleoyl-arachidonoyl-glycerol (18:1/20:4) | Lipid | Diacylglycerol | 0.110572 | 0.000651 |
| linoleoyl-linolenoyl-glycerol (18:2/18:3) | Lipid | Diacylglycerol | 0.316096 | 0.045823 |

TABLE 6-continued 87 significantly different metabolites (p < 0.05) between patients with AMD and controls

| Metabolites | SUPER_PATHWAY | SUB_PATHWAY | Odds Ratio (OR) | P value |
|---|---|---|---|---|
| linoleoyl-arachidonoyl-glycerol (18:2/20:4) | Lipid | Diacylglycerol | 0.096173 | 0.000787 |
| linoleoyl-arachidonoyl-glycerol (18:2/20:4) | Lipid | Diacylglycerol | 0.180502 | 0.00388 |
| linoleoyl-docosahexaenoyl-glycerol (18:2/22:6) | Lipid | Diacylglycerol | 0.302671 | 0.02253 |
| 1-linoleoyl-GPA (18:2) | Lipid | Lysophospholipid | 5.206604 | 0.03694 |
| 1-palmitoyl-2-palmitoleoyl-GPC (16:0/16:1) | Lipid | Phosphatidylcholine (PC) | 0.12779 | 0.008062 |
| 1-palmitoyl-2-stearoyl-GPC (16:0/18:0) | Lipid | Phosphatidylcholine (PC) | 0.103985 | 0.017079 |
| 1-palmitoyl-2-oleoyl-GPC (16:0/18:1) | Lipid | Phosphatidylcholine (PC) | 0.012929 | 0.005146 |
| 1-palmitoyl-2-gamma-linolenoyl-GPC (16:0/18:3n6) | Lipid | Phosphatidylcholine (PC) | 0.209957 | 0.006774 |
| 1-palmitoyl-2-arachidonoyl-GPC (16:0/20:4n6) | Lipid | Phosphatidylcholine (PC) | 0.000449 | 0.000602 |
| 1-stearoyl-2-oleoyl-GPC (18:0/18:1) | Lipid | Phosphatidylcholine (PC) | 0.036914 | 0.007383 |
| 1-stearoyl-2-arachidonoyl-GPC (18:0/20:4) | Lipid | Phosphatidylcholine (PC) | 0.000221 | 0.000523 |
| 1-linoleoyl-2-arachidonoyl-GPC (18:2/20:4n6) | Lipid | Phosphatidylcholine (PC) | 0.046188 | 0.009727 |
| 1-stearoyl-2-arachidonoyl-GPE (18:0/20:4) | Lipid | Phosphatidylethanolamine (PE) | 0.124833 | 0.00735 |
| 1-palmitoyl-2-oleoyl-GPI (16:0/18:1) | Lipid | Phosphatidylinositol (PI) | 0.255201 | 0.022321 |
| 1-palmitoyl-2-arachidonoyl-GPI (16:0/20:4) | Lipid | Phosphatidylinositol (PI) | 0.227191 | 0.018771 |
| 1-stearoyl-2-linoleoyl-GPI (18:0/18:2) | Lipid | Phosphatidylinositol (PI) | 0.229045 | 0.035322 |
| 1-stearoyl-2-arachidonoyl-GPI (18:0/20:4) | Lipid | Phosphatidylinositol (PI) | 0.066444 | 0.004541 |
| 2-palmitoleoyl-GPC (16:1) | Lipid | Lysophospholipid | 0.395601 | 0.040388 |
| 1-linoleoyl-GPC (18:2) | Lipid | Lysophospholipid | 42.49438 | 0.024739 |
| 1-(1-enyl-palmitoyl)-GPC (P-16:0) | Lipid | Lysoplasmalogen | 5.394543 | 0.007327 |
| 1-(1-enyl-palmitoyl)-2-linoleoyl-GPE (P-16:0/18:2) | Lipid | Plasmalogen | 12.33243 | 0.002728 |
| 1-arachidonoyl-GPE (20:4n6) | Lipid | Lysophospholipid | 0.194043 | 0.043161 |
| 1-palmitoleoylglycerol (16:1) | Lipid | Monoacylglycerol | 0.252126 | 0.026776 |
| 2-palmitoleoylglycerol (16:1) | Lipid | Monoacylglycerol | 0.339402 | 0.044798 |
| 3-hydroxybutyrylcarnitine (1) | Lipid | Fatty Acid Metabolism(Acyl Carnitine) | 0.343344 | 0.03374 |
| leucylglutamine | Peptide | Dipeptide | 2.86657 | 0.0108 |
| leucylglycine | Peptide | Dipeptide | 2.454582 | 0.022602 |
| valylglutamine | Peptide | Dipeptide | 3.409627 | 0.016234 |
| valylglycine | Peptide | Dipeptide | 2.577158 | 0.03962 |
| glutamate, gamma-methyl ester | Amino Acid | Glutamate Metabolism | 4.361219 | 0.048854 |
| stearoyl-arachidonoyl-glycerol (18:0/20:4) | Lipid | Diacylglycerol | 0.041122 | 0.000886 |
| 1-(1-enyl-palmitoyl)-GPE (P-16:0) | Lipid | Lysoplasmalogen | 8.00629 | 0.002486 |
| 1-(1-enyl-oleoyl)-GPE (P-18:1) | Lipid | Lysoplasmalogen | 6.890958 | 0.002603 |
| 1-(1-enyl-stearoyl)-GPE (P-18:0) | Lipid | Lysoplasmalogen | 6.807911 | 0.00342 |
| arachidonoylcarnitine (C20:4) | Lipid | Fatty Acid Metabolism(Acyl Carnitine) | 0.128372 | 0.005885 |

TABLE 6-continued 87 significantly different metabolites (p < 0.05) between patients with AMD and controls

| Metabolites | SUPER_PATHWAY | SUB_PATHWAY | Odds Ratio (OR) | P value |
|---|---|---|---|---|
| adrenoylcarnitine (C22:4) | Lipid | Fatty Acid Metabolism(Acyl Carnitine) | 0.144019 | 0.005925 |
| ximenoylcarnitine (C26:1) | Lipid | Fatty Acid Metabolism(Acyl Carnitine) | 0.147658 | 0.008655 |
| linoleoylcholine | Lipid | Fatty Acid Metabolism (Acyl Choline) | 4.839919 | 0.011516 |
| diacylglycerol (16:1/18:2, 16:0/18:3) | Lipid | Diacylglycerol | 0.283027 | 0.012983 |
| nervonoylcarnitine (C24:1) | Lipid | Fatty Acid Metabolism(Acyl Carnitine) | 0.121618 | 0.01734 |
| lignoceroylcarnitine (C24) | Lipid | Fatty Acid Metabolism(Acyl Carnitine) | 0.215983 | 0.017833 |
| dihomo-linolenoylcarnitine (20:3n3 or 6) | Lipid | Fatty Acid Metabolism(Acyl Carnitine) | 0.186428 | 0.020052 |
| 5alpha-androstan-3alpha,17beta-diol monosulfate (2) | Lipid | Steroid | 3.560437 | 0.021243 |
| 1-stearoyl-2-oleoyl-GPI (18:0/18:1) | Lipid | Phosphatidylinositol (PI) | 0.256254 | 0.022469 |
| palmitoleoylcarnitine (C16:1) | Lipid | Fatty Acid Metabolism(Acyl Carnitine) | 0.273249 | 0.026832 |
| 14-HDoHE/17-HDoHE | Lipid | Fatty Acid, Monohydroxy | 0.352353 | 0.034334 |
| myristoleoylcarnitine (C14:1) | Lipid | Fatty Acid Metabolism(Acyl Carnitine) | 0.34993 | 0.035743 |
| sphingomyelin (d18:1/20:1, d18:2/20:0)* | Lipid | Sphingolipid Metabolism | 7.224073 | 0.035917 |
| dihomo-linoleoylcarnitine (C20:2) | Lipid | Fatty Acid Metabolism(Acyl Carnitine) | 0.236561 | 0.038979 |
| 5alpha-androstan-3alpha,17beta-diol disulfate | Lipid | Steroid | 2.441771 | 0.042251 |

TABLE 7

33 significantly different metabolites (p < 0.01) between patients with AMD and controls

| Metabolites | OR | P value |
|---|---|---|
| oleoyl-arachidonoyl-glycerol (18:1/20:4) | 0.046336 | 0.000159 |
| 1-stearoyl-2-arachidonoyl-GPC (18:0/20:4) | 0.000221 | 0.000523 |
| 1-palmitoyl-2-arachidonoyl-GPC (16:0/20:4n6) | 0.000449 | 0.000602 |
| oleoyl-arachidonoyl-glycerol (18:1/20:4) | 0.110572 | 0.000651 |
| linoleoyl-arachidonoyl-glycerol (18:2/20:4) | 0.096173 | 0.000787 |
| stearoyl-arachidonoyl-glycerol (18:0/20:4) | 0.041122 | 0.000886 |
| adenosine | 3.742296 | 0.000913 |
| 1-(1-enyl-palmitoyl)-GPE (P-16:0) | 8.00629 | 0.002486 |
| 1-(1-enyl-oleoyl)-GPE (P-18:1) | 6.890958 | 0.002603 |
| 1-(1-enyl-palmitoyl)-2-linoleoyl-GPE (P-16:0/18:2) | 12.33243 | 0.002728 |
| cysteine s-sulfate | 0.153389 | 0.003077 |
| adenosine 5'-monophosphate (AMP) | 3.271218 | 0.003173 |
| 1-(1-enyl-stearoyl)-GPE (P-18:0) | 6.807911 | 0.00342 |
| palmitoyl-arachidonoyl-glycerol (16:0/20:4) | 0.192538 | 0.003875 |
| linoleoyl-arachidonoyl-glycerol (18:2/20:4) | 0.180502 | 0.00388 |
| 1-stearoyl-2-arachidonoyl-GPI (18:0/20:4) | 0.066444 | 0.004541 |
| 1-palmitoyl-2-oleoyl-GPC (16:0/18:1) | 0.012929 | 0.005146 |
| arachidonoylcarnitine (C20:4) | 0.128372 | 0.005885 |
| adrenoylcarnitine (C22:4) | 0.144019 | 0.005925 |
| stearoylcarnitine (C18) | 0.160933 | 0.006154 |
| 1-palmitoyl-2-gamma-linolenoyl-GPC (16:0/18:3n6) | 0.209957 | 0.006774 |
| palmitoyl-arachidonoyl-glycerol (16:0/20:4) | 0.252937 | 0.0071 |
| 1-(1-enyl-palmitoyl)-GPC (P-16:0) | 5.394543 | 0.007327 |
| 1-stearoyl-2-arachidonoyl-GPE (18:0/20:4) | 0.124833 | 0.00735 |
| 1-stearoyl-2-oleoyl-GPC (18:0/18:1) | 0.036914 | 0.007383 |

TABLE 7-continued 33 significantly different metabolites (p < 0.01) between patients with AMD and controls

| Metabolites | OR | P value |
|---|---|---|
| 1-palmitoyl-2-palmitoleoyl-GPC (16:0/16:1) | 0.12779 | 0.008062 |
| ximenoylcarnitine (C26:1) | 0.147658 | 0.008655 |
| alpha-tocopherol | 11.84447 | 0.009147 |
| palmitoyl-linoleoyl-glycerol (16:0/18:2) | 0.27047 | 0.009372 |
| biliverdin | 7.503205 | 0.009436 |
| 1-linoleoyl-2-arachidonoyl-GPC (18:2/20:4n6) | 0.046188 | 0.009727 |
| 1-palmitoyl-2-arachidonoyl-GPE (16:0/20:4) | 0.169948 | 0.009794 |
| palmitoleoyl-linoleoyl-glycerol (16:1/18:2) | 0.250453 | 0.009831 |

TABLE 8

48 metabolites that were significantly different across the different stages of AMD

| Metabolites | SUPER_PATHWAY | SUB_PATHWAY | P |
|---|---|---|---|
| 1-stearoyl-2-oleoyl-GPC (18:0/18:1) | Lipid | Phosphatidylcholine (PC) | 0.001916 |
| 1-linoleoyl-2-arachidonoyl-GPC (18:2/20:4n6) | Lipid | Phosphatidylcholine (PC) | 0.002356 |
| stearoyl-arachidonoyl-glycerol (18:0/20:4) | Lipid | Diacylglycerol | 0.002415 |
| oleoyl-oleoyl-glycerol (18:1/18:1) | Lipid | Diacylglycerol | 0.003115 |
| dihomo-linolenoyl carnitine (20:3n3 or 6) | Lipid | Fatty Acid Metabolism(Acyl Carnitine) | 0.003929 |
| 1-stearoyl-2-arachidonoyl-GPC (18:0/20:4) | Lipid | Phosphatidylcholine (PC) | 0.004266 |
| linoleoyl-linolenoyl-glycerol (18:2/18:3) | Lipid | Diacylglycerol | 0.004286 |
| 1-stearoyl-2-linoleoyl-GPI (18:0/18:2) | Lipid | Phosphatidylinositol (PI) | 0.007734 |
| N2-methylguanosine | Nucleotide | Purine Metabolism, Guanine containing | 0.00788 |
| oleoyl-linoleoyl-glycerol (18:1/18:2) | Lipid | Diacylglycerol | 0.007984 |
| oleoylcarnitine (C18:1) | Lipid | Fatty Acid Metabolism(Acyl Carnitine) | 0.00803 |
| ximenoylcarnitine (C26:1) | Lipid | Fatty Acid Metabolism(Acyl Carnitine) | 0.008773 |
| 1-stearoyl-2-arachidonoyl-GPI (18:0/20:4) | Lipid | Phosphatidylinositol (PI) | 0.009111 |
| lignoceroylcarnitine (C24) | Lipid | Fatty Acid Metabolism(Acyl Carnitine) | 0.012431 |
| myristoylcarnitine (C14) | Lipid | Fatty Acid Metabolism(Acyl Carnitine) | 0.01285 |
| 1-stearoyl-2-oleoyl-GPI (18:0/18:1) | Lipid | Phosphatidylinositol (PI) | 0.015297 |
| 1-palmitoyl-2-arachidonoyl-GPC (16:0/20:4n6) | Lipid | Phosphatidylcholine (PC) | 0.016341 |
| oleoyl-linoleoyl-glycerol (18:1/18:2) | Lipid | Diacylglycerol | 0.018107 |
| 1-palmitoyl-2-stearoyl-GPC (16:0/18:0) | Lipid | Phosphatidylcholine (PC) | 0.018298 |
| linoleoyl-arachidonoyl-glycerol (18:2/20:4) | Lipid | Diacylglycerol | 0.018949 |
| palmitoylcarnitine (C16) | Lipid | Fatty Acid Metabolism(Acyl Carnitine) | 0.019802 |
| linoleoyl-arachidonoyl-glycerol (18:2/20:4) | Lipid | Diacylglycerol | 0.02055 |
| cerotoylcarnitine (C26) | Lipid | Fatty Acid Metabolism(Acyl Carnitine) | 0.020642 |
| palmitoyl-oleoyl-glycerol (16:0/18:1) | Lipid | Diacylglycerol | 0.020832 |
| biliverdin | Cofactors and Vitamins | Hemoglobin and Porphyrin Metabolism | 0.021241 |
| diacylglycerol (16:1/18:2, 16:0/18:3) | Lipid | Diacylglycerol | 0.021689 |
| laurylcarnitine (C12) | Lipid | Fatty Acid Metabolism(Acyl Carnitine) | 0.021767 |
| adenosine | Nucleotide | Purine Metabolism, Adenine containing | 0.022683 |

TABLE 8-continued 48 metabolites that were significantly different across the different stages of AMD

| Metabolites | SUPER_PATHWAY | SUB_PATHWAY | P |
|---|---|---|---|
| isovalerate | Amino Acid | Leucine, Isoleucine and Valine Metabolism | 0.023621 |
| arachidonoylcarnitine (C20:4) | Lipid | Fatty Acid Metabolism(Acyl Carnitine) | 0.023665 |
| N-acetylasparagine | Amino Acid | Alanine and Aspartate Metabolism | 0.023823 |
| oleoyl-arachidonoyl-glycerol (18:1/20:4) | Lipid | Diacylglycerol | 0.024198 |
| palmitoleoylcarnitine (C16:1) | Lipid | Fatty Acid Metabolism(Acyl Carnitine) | 0.025781 |
| myristoleoylcarnitine (C14:1) | Lipid | Fatty Acid Metabolism(Acyl Carnitine) | 0.026779 |
| adrenoylcarnitine (C22:4) | Lipid | Fatty Acid Metabolism(Acyl Carnitine) | 0.029296 |
| 1-(1-enyl-palmitoyl)-GPC (P-16:0) | Lipid | Lysoplasmalogen | 0.030468 |
| 1-palmitoyl-2-oleoyl-GPC (16:0/18:1) | Lipid | Phosphatidylcholine (PC) | 0.032047 |
| cysteine s-sulfate | Amino Acid | Methionine, Cysteine, SAM and Taurine Metabolism | 0.036799 |
| dihomo-linoleoylcarnitine (C20:2) | Lipid | Fatty Acid Metabolism(Acyl Carnitine) | 0.037441 |
| alpha-tocopherol | Cofactors and Vitamins | Tocopherol Metabolism | 0.038148 |
| oleoyl-arachidonoyl-glycerol (18:1/20:4) | Lipid | Diacylglycerol | 0.038152 |
| 1-palmitoyl-2-arachidonoyl-GPI (16:0/20:4) | Lipid | Phosphatidylinositol (PI) | 0.03856 |
| 1-(1-enyl-palmitoyl)-GPE (P-16:0) | Lipid | Lysoplasmalogen | 0.039209 |
| 1-(1-enyl-stearoyl)-GPE (P-18:0) | Lipid | Lysoplasmalogen | 0.039528 |
| 1-palmitoyl-2-oleoyl-GPI (16:0/18:1) | Lipid | Phosphatidylinositol (PI) | 0.042278 |
| stearoylcarnitine (C18) | Lipid | Fatty Acid Metabolism(Acyl Carnitine) | 0.043316 |
| palmitoleoyl-linoleoyl-glycerol (16:1/18:2) | Lipid | Diacylglycerol | 0.044462 |
| palmitoyl-linoleoyl-glycerol (16:0/18:2) | Lipid | Diacylglycerol | 0.049741 |

Metabolite set enrichment of these 87 metabolites supported the results of the PC analysis, by confirming the importance of lipid metabolism, specifically glycerophospholipid metabolism, in AMD. Indeed, this pathway was highly enriched among the significant metabolites (p=4.7× $10^{-9}$).

ROC Curve Analysis

Figure 2:
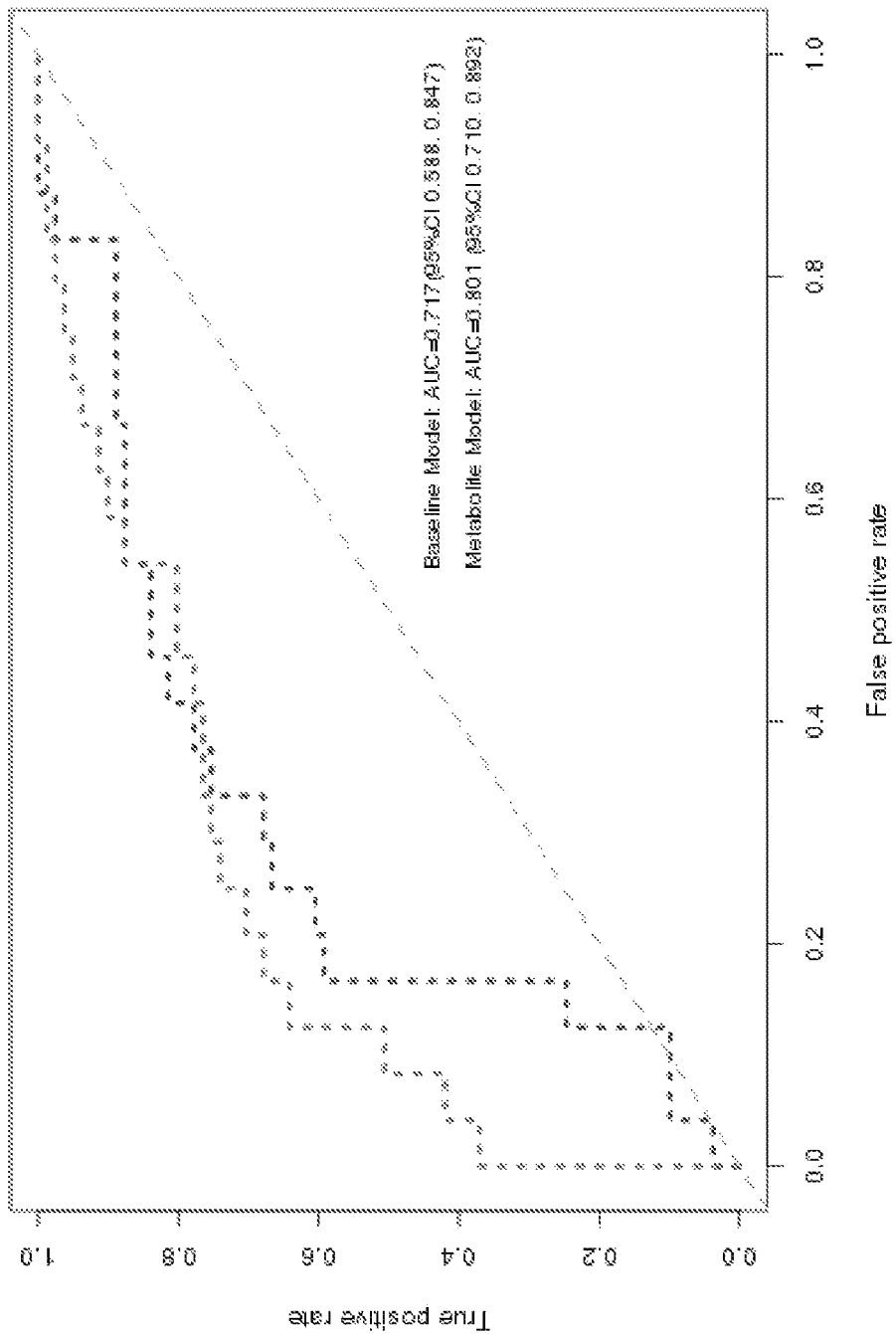
FIG. 2 is a graph showing a receiver operating characteristic (ROC) curve analysis of a model including the 87 significant metabolites as compared to the baseline model.

The significant features identified in the multivariate logistic regression were used to create a predictive model for AMD, which was assessed using ROC curve analyses. When the first principal component of these 87 features was included as a model predictor, ROC analysis (AUC: 0.80; 95% CI: 0.71, 0.90; p=0.142) showed that it outperformed a baseline model including only age, gender, BMI and smoking status (AUC: 0.71, 0.59, 0.85). In FIG. 2, the red line indicates the results of the ROC analysis for the predictive model including metabolites data, and the blue line indicates the results of the ROC analysis for the baseline model including only age, gender, BMI, and smoking status.

ANOVA Analysis

Analyses were further performed to determine whether the identified significant metabolites were able to discriminate between early, intermediate and late stage AMD cases. ANOVA analysis revealed that, of the 87 metabolites, 48 (55.2%) were significantly different across the different stages of AMD (Table 8). Consistent with the previous data, all but one of the 13 most significant metabolites (p<0.01) belonged to the lipid pathways (diacylglycerol n=4; phosphatidylcholine n=3; fatty acid metabolism n=3; phosphatidylinositol n=2). FIG. 3 displays the mean peak intensity of these 13 metabolites across the three AMD groups. Similarly to what has been observed for the comparison between AMD and controls, metabolite set enrichment analysis of the 48 metabolites that significantly differed among the three AMD groups revealed an enrichment of glycerophospholipids pathway (p=0.01).

In conclusion, levels of plasma metabolites are associated with AMD, and different severity stages. Using UPLC-MS, 878 biochemicals were identified. Multivariate logistic regression identified 87 metabolites significantly different between patients with AMD and controls. Most of these metabolites (81.6%, n=71) belonged to the lipid pathways. ANOVA analysis revealed that of the 87 metabolites, 48 (55.2%) were also significantly different across the different stages of AMD. Of the 7 metabolites showing greatest significant differences (p<0.001), all but one were lipids. A significant enrichment of glycerophospholipids pathway was identified (p=4.7×$10^{-9}$). The data for the first time provides a comprehensive overview of AMD metabolomics, and suggest that MS plasma metabolomic profiling is a powerful tool to identify subjects with AMD and to distinguish the different stages of disease. These findings also contribute to the current knowledge on AMD pathophysiology, by highlighting the possible role of lipid metabolism. The data suggests that the most relevant metabolites map to the glycerophospholipid pathway. These findings offer novel targets for early diagnosis, monitoring and treatment of AMD, in order to prevent vision loss associated with this blinding disease.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating Age-related Macular Degeneration (AMD) in a subject, the method comprising:
   (a) obtaining a sample from the subject;
   (b) performing mass spectrometry on the sample to determine the amount of a set of metabolites in the sample;
   (c) applying a principal component algorithm to a dataset derived from the level of the set of metabolites, thereby obtaining a value corresponding to one or more principal components for the subject;
   (d) determining that the value corresponding to the one or more principal components for the subject is associated with AMD, thus determining that the subject has AMD;
   (e) administering a treatment to the subject, wherein the treatment is an anti-VEGF agent or an antioxidant vitamin,
   wherein the set of metabolites comprises one or more of the metabolites in Table 5, Table 6, or Table 7.

2. The method of claim 1, wherein the sample is a serum sample or a urine sample.

3. The method of claim 1, further comprising determining the stage of AMD in the subject by determining the amount of a set of metabolites in the sample, wherein the set of metabolites comprises one or more metabolites in Table 8, wherein, depending on the one or more metabolites:
   (i) an increased level of the one or more metabolites compared to levels found in healthy subjects or in subjects with early stage AMD is associated with more severe AMD; or
   (ii) a decreased level of the one or more metabolites compared to levels found in healthy subjects or in subjects with early stage AMD is associated with more severe AMD.

4. The method of claim 3, wherein the set of metabolites comprises 1-stearoyl-2-oleoyl-GPC, 1-linoleoyl-2-arachidonoyl-GPC, stearoyl-arachidonoyl-glycerol, oleoyl-oleoyl-glycerol, dihomo-linolenoylcarnitine, 1-stearoyl-2-arachidonoyl-GPC, linoleoyl-linolenoyl-glycerol, 1-stearoyl-2-linoleoyl-GPI, N2-methylguanosine, oleoyl-linoleoyl-glycerol, oleoylcarnitine, ximenoylcarnitine, or 1-stearoyl-2-arachidonoyl-GPI.

5. The method of claim 3, wherein the sample is a serum sample or a urine sample.

6. The method of claim 3, wherein the stage of AMD is determined by principal component analysis.

7. The method of claim 3, wherein the stage of AMD is determined by regression analysis.

8. A method of treating Age-related Macular Degeneration (AMD) in a subject, the method comprising:
   (a) obtaining a sample from the subject;
   (b) performing mass spectrometry on the sample to determine the amount of a set of metabolites in the sample; and
   (c) determining that the amount of one or more metabolites selected from the group consisting of linoleoyl-arachidonoyl-glycerol, stearoyl-arachidonoyl-glycerol, oleoyl-arachidonoyl-glycerol, oleoyl-arachidonoyl-glycerol, 1-palmitoyl-2-arachidonoyl-GPC, and 1-stearoyl-2-arachidonoyl-GPC is lower than a reference value; or
   determining that the amount of adenosine is higher than a reference value;
   (d) determining that the subject has AMD;
   (e) administering a treatment to the subject, wherein the treatment is an anti-VEGF agent or an antioxidant vitamin.

9. The method of claim 8, wherein the sample is a serum sample or a urine sample.

10. The method of claim 8, further comprising determining the stage of AMD in the subject by determining the amount of a set of metabolites in the sample, wherein the set of metabolites comprises one or more metabolites in Table 8, wherein, depending on the one or more metabolites:
    (i) an increased level of the one or more metabolites compared to levels found in healthy subjects or in subjects with early stage AMD is associated with more severe AMD; or
    (ii) a decreased level of the one or more metabolites compared to levels found in healthy subjects or in subjects with early stage AMD is associated with more severe AMD.

11. The method of claim 10, wherein the set of metabolites comprises 1-stearoyl-2-oleoyl-GPC, 1-linoleoyl-2-arachidonoyl-GPC, stearoyl-arachidonoyl-glycerol, oleoyl-oleoyl-glycerol, dihomo-linolenoylcarnitine, 1-stearoyl-2-arachidonoyl-GPC, linoleoyl-linolenoyl-glycerol, 1-stearoyl-2-linoleoyl-GPI, N2-methylguanosine, oleoyl-linoleoyl-glycerol, oleoylcarnitine, ximenoylcarnitine, or 1-stearoyl-2-arachidonoyl-GPI.

12. The method of claim 10, wherein the sample is a serum sample or a urine sample.

13. The method of claim 10, wherein the stage of AMD is determined by principal component analysis.

14. The method of claim 10, wherein the stage of AMD is determined by regression analysis.

* * * * *

UNITED STATES PATENT AND TRADEMARK OFFICE
CERTIFICATE OF CORRECTION

| | |
|---|---|
| PATENT NO. | : 11,789,024 B2 |
| APPLICATION NO. | : 16/612099 |
| DATED | : October 17, 2023 |
| INVENTOR(S) | : Ines Maria de Carvalho Lains et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 888 days.

Signed and Sealed this
Twelfth Day of November, 2024

*Katherine Kelly Vidal*

Katherine Kelly Vidal
*Director of the United States Patent and Trademark Office*